US008431579B2

(12) United States Patent
Johnson et al.

(10) Patent No.: US 8,431,579 B2
(45) Date of Patent: *Apr. 30, 2013

(54) CAPPED PYRAZINOYLGUANIDINE SODIUM CHANNEL BLOCKERS

(75) Inventors: Michael R. Johnson, Chapel Hill, NC (US); Bruce F. Molino, Slingerlands, NY (US); Jianzhong Zhang, Rensselaer, NY (US); Bruce Sargent, Delmar, NY (US)

(73) Assignee: Parion Sciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,579

(22) Filed: Nov. 4, 2010

(65) Prior Publication Data

US 2011/0046158 A1 Feb. 24, 2011

Related U.S. Application Data

(60) Continuation of application No. 12/049,968, filed on Mar. 17, 2008, now Pat. No. 7,868,010, which is a division of application No. 11/138,280, filed on May 27, 2005, now Pat. No. 7,388,013, which is a continuation of application No. 10/920,410, filed on Aug. 18, 2004, now Pat. No. 7,064, 129.

(60) Provisional application No. 60/495,725, filed on Aug. 18, 2003.

(51) Int. Cl.
*A61K 31/4965* (2006.01)

(52) U.S. Cl.
USPC ..................................... 514/255.06; 544/407

(58) Field of Classification Search ............. 514/255.06; 544/407
See application file for complete search history.

(56) References Cited

U.S. PATENT DOCUMENTS

| | | | |
|---|---|---|---|
| 3,313,813 | A | 4/1967 | Cragoe, Jr. |
| 3,527,758 | A | 9/1970 | Cragoe, Jr., et al. |
| 4,246,406 | A | 1/1981 | Cragoe, Jr. et al. |
| 6,858,614 | B2 | 2/2005 | Johnson |
| 6,858,615 | B2 | 2/2005 | Johnson |
| 6,903,105 | B2 | 6/2005 | Johnson |
| 6,995,160 | B2 | 2/2006 | Johnson |
| 7,026,325 | B2 | 4/2006 | Johnson |
| 7,030,117 | B2 | 4/2006 | Johnson |
| 7,064,129 | B2 | 6/2006 | Johnson et al. |
| 7,186,833 | B2 | 3/2007 | Johnson |
| 7,189,719 | B2 | 3/2007 | Johnson |
| 7,192,958 | B2 | 3/2007 | Johnson |
| 7,192,959 | B2 | 3/2007 | Johnson |
| 7,192,960 | B2 | 3/2007 | Johnson |
| 7,241,766 | B2 | 7/2007 | Johnson |
| 7,247,636 | B2 | 7/2007 | Johnson |
| 7,247,637 | B2 | 7/2007 | Johnson et al. |
| 7,317,013 | B2 | 1/2008 | Johnson |
| 7,332,496 | B2 | 2/2008 | Johnson |
| 7,345,044 | B2 | 3/2008 | Johnson |
| 7,368,447 | B2 | 5/2008 | Johnson et al. |
| 7,368,450 | B2 | 5/2008 | Johnson |
| 7,368,451 | B2 | 5/2008 | Johnson et al. |
| 7,375,107 | B2 | 5/2008 | Johnson |
| 7,388,013 | B2 | 6/2008 | Johnson et al. |
| 7,399,766 | B2 | 7/2008 | Johnson |
| 7,410,968 | B2 | 8/2008 | Johnson et al. |
| 7,745,442 | B2 | 6/2010 | Johnson et al. |
| 7,807,834 | B2 | 10/2010 | Johnson et al. |
| 7,820,678 | B2 | 10/2010 | Johnson |
| 7,842,697 | B2 | 11/2010 | Johnson |
| 7,868,010 | B2 | 1/2011 | Johnson et al. |
| 2005/0090505 | A1 | 4/2005 | Johnson et al. |
| 2006/0142306 | A1 | 6/2006 | Johnson |
| 2006/0142581 | A1 | 6/2006 | Johnson |
| 2007/0265280 | A1 | 11/2007 | Johnson |
| 2008/0090841 | A1 | 4/2008 | Johnson et al. |
| 2008/0096896 | A1 | 4/2008 | Johnson |
| 2008/0103148 | A1 | 5/2008 | Johnson |
| 2008/0167466 | A1 | 7/2008 | Johnson et al. |
| 2008/0171879 | A1 | 7/2008 | Johnson |
| 2008/0176863 | A1 | 7/2008 | Johnson et al. |
| 2008/0177072 | A1 | 7/2008 | Johnson |
| 2008/0200476 | A1 | 8/2008 | Johnson |
| 2008/0249109 | A1 | 10/2008 | Johnson et al. |
| 2008/0293740 | A1 | 11/2008 | Johnson et al. |
| 2009/0018144 | A1 | 1/2009 | Johnson et al. |
| 2009/0062308 | A1 | 3/2009 | Johnson |
| 2009/0082287 | A1 | 3/2009 | Johnson et al. |

(Continued)

FOREIGN PATENT DOCUMENTS

| | | | |
|---|---|---|---|
| AU | 2003211135 | A1 | 9/2003 |
| AU | 2004212962 | A1 | 9/2004 |

(Continued)

OTHER PUBLICATIONS

European Office Action in Application No. 04781545.1 dated Sep. 10, 2010.

(Continued)

*Primary Examiner* — Douglas M Willis
(74) *Attorney, Agent, or Firm* — Oblon, Spivak, McClelland, Maier & Neustadt, L.L.P.

(57) ABSTRACT

Provided are compounds represented by the formula:

(I)

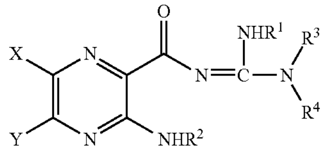

where the structural variables are as defined herein. The compounds function as sodium channel blockers and my be used for promoting hydration of mucosal surfaces.

19 Claims, No Drawings

U.S. PATENT DOCUMENTS

| | | | |
|---|---|---|---|
| 2009/0104272 | A1 | 4/2009 | Boucher et al. |
| 2009/0214444 | A1 | 8/2009 | Johnson |
| 2009/0227530 | A1 | 9/2009 | Johnson |
| 2009/0227594 | A1 | 9/2009 | Johnson |
| 2009/0253714 | A1 | 10/2009 | Johnson et al. |
| 2009/0324724 | A1 | 12/2009 | Johnson |
| 2010/0074881 | A1 | 3/2010 | Boucher et al. |
| 2010/0144661 | A1 | 6/2010 | Johnson |
| 2010/0267746 | A1 | 10/2010 | Johnson |
| 2011/0003832 | A1 | 1/2011 | Johnson et al. |
| 2011/0008268 | A1 | 1/2011 | Johnson et al. |

FOREIGN PATENT DOCUMENTS

| | | |
|---|---|---|
| WO | WO 03/070182 | 8/2003 |
| WO | WO 03/070182 A2 | 8/2003 |
| WO | WO 03/070182 A3 | 8/2003 |
| WO | WO 2004/073629 | 9/2004 |

OTHER PUBLICATIONS

Supplementary European Search Report in Application No. 04781545 dated Oct. 3, 2008.
Canadian Office Action in co-pending Application No. 2,534,682 dated Mar. 10, 2011.
Notice of Grounds for Rejection in co-pending Korean Application No. 10-2006-7003333 dated May 13, 2011.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 11/696,003, filed Apr. 3, 2007, Johnson.
U.S. Appl. No. 60/909,818, filed Apr. 3, 2007, Johnson, et al.
U.S. Appl. No. 60/909,802, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al.
U.S. Appl. No. 11/835,902, filed Aug. 8, 2007, Johnson, et al.
U.S. Appl. No. 61/030,313, filed Feb. 21, 2008, Johnson.
U.S. Appl. No. 61/031,466, filed Feb. 26, 2008, Johnson.
U.S. Appl. No. 12/171,867, filed Jul. 11, 2008, Johnson, et al.
U.S. Appl. No. 12/171,897, filed Jul. 11, 2008, Johnson, et al.
U.S. Appl. No. 60/079,989, filed Jul. 11, 2008, Boucher, et al.
U.S. Appl. No. 12/304,042, filed Dec. 9, 2008, Johnson.
Office Action issued Jan. 17, 2011 in Australia Application No. 2004266704.
Office Action issued Apr. 1, 2011, in European Patent Application No. 04 781 545.1-2117.
European Office Action in Corresponding European Application No. 04 781 545.1-2117, dated Dec. 2, 2011.
Examiner's Report No. 3 in patent Application No. 2004266704 dated Jan. 19, 2012.
U.S. Appl. No. 13/353,018, filed Jan. 18, 2012, Johnson.
Extended European Search Report issued May 11, 2012 in patent application No. 12159292.7.
U.S. Appl. No. 13/467,618, filed May 9, 2012, Johnson, et al.
U.S. Appl. No. 13/492,711, filed Jun. 8, 2012, Johnson, et al.
U.S. Appl. No. 13/533,911, filed Jun. 26, 2012, Johnson.
Office Action issued Jun. 25, 2012 in European Application No. 12159292.7.
U.S. Appl. No. 13/669,822, filed Nov. 6, 2012, Johnson.

CAPPED PYRAZINOYLGUANIDINE SODIUM CHANNEL BLOCKERS

CONTINUING APPLICATION DATA

This application is a Continuation of U.S. application Ser. No. 12/049,968, now allowed, which is a Divisional of U.S. application Ser. No. 11/138,280, filed on May 27, 2005, which is a Continuation of U.S. application Ser. No. 10/920,410, filed on Aug. 18, 2004, which claims benefit to Provisional Application Ser. No. 60/495,725, filed Aug. 18, 2003.

BACKGROUND OF THE INVENTION

1. Field of the Invention

The present invention relates to sodium channel blockers. The present invention also includes a variety of methods of treatment using these inventive sodium channel blockers.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of rehydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diurectics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete Cl— (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

Fifty million Americans and hundreds of millions of others around the world suffer from high blood pressure and the subsequent sequale leading to congestive heart failure and increasing mortality. It is the Western World's leading killer and there is a need there for new medicines to treat these diseases. Thus, in addition, some of the novel sodium channel blockers of this invention can be designed to target the kidney and as such they may be used as diuretics for the treatment of hypertension, congestive heart failure (CHF) and other cardiovascular diseases. These new agents may be used alone or in combination with beta-blockers, ACE inhibitors, HMG-CoA reductase inhibitors, calcium channel blockers and other cardiovascular agents.

SUMMARY OF THE INVENTION

It is an object of the present invention to provide compounds that are more potent and/or absorbed less rapidly from mucosal surfaces, and/or are less reversible as compared to known compounds.

It is another aspect of the present invention to provide compounds that are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds.

It is another object of the present invention to provide compounds which are (1) absorbed less rapidly from mucosal surfaces, especially airway surfaces, as compared to known compounds and; (2) when absorbed from musosal surfaces after administration to the mucosal surfaces, are converted in vivo into metabolic derivatives thereof which have reduced efficacy in blocking sodium channels as compared to the administered parent compound. It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on mucosal surfaces as compared to previous compounds.

It is another object of the present invention to provide compounds that target the kidney for use in the treatment of cardiovascular disease.

It is another object of the present invention to provide methods of treatment that take advantage of the pharmacological properties of the compounds described above.

In particular, it is an object of the present invention to provide methods of treatment which rely on rehydration of mucosal surfaces.

In particular, it is an object of the present invention to provide methods of treating cardiovascular disease.

The objects of the present invention may be accomplished with a class of pyrazinoylguanidine compounds represented by formula (I):

(I)

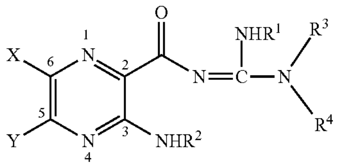

wherein

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $—N(R^2)_2$;

$R^1$ is hydrogen or lower alkyl;

each $R^2$ is, independently, $—R^7$, $—(CH_2)_m—OR^8$, $—(CH_2)_m—NR^7R^{10}$, $—(CH_2)_n(CHOR^8)(CHOR^8)_n—CH_2OR^8$, $—(CH_2CH_2O)_m—R^8$, $—(CH_2CH_2O)_m—CH_2CH_2NR^7R^{10}$, $—(CH_2)_n—C(=O)NR^7R^{10}$, $—(CH_2)_n—Z_g—R^7$, $—(CH_2)_m—NR^{10}—CH_2(CHOR^8)(CHOR^8)_n—CH_2OR^8$, $—(CH_2)_n—CO_2R^7$, or

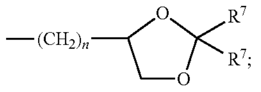

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

(A)

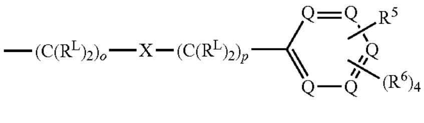

wherein each $R^L$ is, independently, $—R^7$, $—(CH_2)_n—OR^8$, $—O—(CH_2)_m—OR^8$, $—(CH_2)_n—NR^7R^{10}$, $—O—(CH_2)_m—NR^7R^{10}$, $—(CH_2)_n(CHOR^8)(CHOR^8)_n—CH_2OR^8$, $—O—(CH_2)_m(CHOR^8)(CHOR^8)_n—CH_2OR^8$, $—(CH_2CH_2O)_m—R^8$, $—O—(CH_2CH_2O)_m—R^8$, $—(CH_2CH_2O)_m—CH_2CH_2NR^7R^{10}$, $—O—(CH_2CH_2O)_m—CH_2CH_2NR^7R^{10}$, $—(CH_2)_n—C(=O)NR^7R^{10}$, $—O—(CH_2)_m—C(=O)NR^7R^{10}$, $—(CH_2)_n—(Z)_g—R^7$, $—O—(CH_2)_m—(Z)_g—R^7$, $—(CH_2)_n—NR^{10}—CH_2(CHOR^8)(CHOR^8)_n—CH_2OR^8$, $—O—(CH_2)_m—NR^{10}—CH_2(CHOR^8)(CHOR^8)_n—$ $CH_2OR^8$, $-(CH_2)_n-CO_2R^7$, $-O-(CH_2)_m-CO_2R^7$, $-OSO_3H$, —O-glucuronide, —O-glucose,

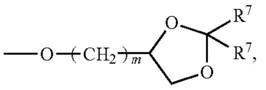

or

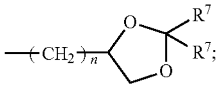

each o is, independently, an integer from 0 to 10;

each p is an integer from 0 to 10;

with the proviso that the sum of o and p in each contiguous chain is from 1 to 10;

each x is, independently, O, $NR^{10}$, C(=O), CHOH, $C(=N-R^{10})$, $CHNR^7R^{10}$, or represents a single bond;

wherein each $R^5$ is, independently, Link $-(CH_2)_n-$CAP, Link $-(CH_2)_n(CHOR^8)(CHOR^8)_n-$CAP, Link $-(CH_2CH_2O)_m-CH_2-$CAP, Link $-(CH_2CH_2O)_m-CH_2CH_2-$CAP, Link $-(CH_2)_n-(Z)_g-$CAP, Link $-(CH_2)_n(Z)_g-(CH_2)_m-$CAP, Link $-(CH_2)_n-NR^{13}-CH_2(CHOR^8)(CHOR^8)_n-$CAP, Link $-(CH_2)_n-(CHOR^8)_mCH_2-NR^{13}-(Z)_g-$CAP, Link $-(CH_2)_nNR^{13}-(CH_2)_m(CHOR^8)_nCH_2NR^{13}-(Z)_g-$CAP, Link $-(CH_2)_m-(Z)_g-(CH_2)_m-$CAP, Link NH—C(=O)—NH—$(CH_2)_m-$CAP, Link $-(CH_2)_m-C(=O)NR^{13}-(CH_2)_m-C(=O)NR^{10}R^{10}$, Link $-(CH_2)_m-C(=O)NR^{13}-(CH_2)_m-$CAP, Link $-(CH_2)_m-C(=O)NR^{11}R^{11}$, Link $-(CH_2)_m-C(=O)NR^{12}R^{12}$, Link $-(CH_2)_n-(Z)_g-(CH_2)_m-(Z)_g-$CAP, Link $-Z_g-(CH_2)_m$-Het-$(CH_2)_m-$CAP.

each Link is, independently, —O—, $-(CH_2)_n-$, $-O(CH_2)_m-$, $-NR^{13}-C(=O)-NR^{13}$, $-NR^{13}-C(=O)-(CH_2)_m-$, $-C(=O)NR^{13}-(CH_2)_m$, $-(CH_2)_n-Z_g-(CH_2)_n$, —S—, —SO—, $-SO_2-$, $-SO_2NR^7-$, $-SO_2NR^{10}-$, or -Het-;

each CAP is, independently, thiazolidinedione, oxazolidinedione, heteroaryl-$C(=O)NR^{13}R^{13}R^{13}$, heteroaryl-W, —CN, $-O-C(=S)NR^{13}R^{13}$, $-Z_gR^{13}$, $-CR^{10}(Z_gR^{13})(Z_gR^{13})$, —C(=O)OAr, $-C(=O)NR^{13}$Ar, imidazoline, tetrazole, tetrazole amide, $-SO_2NHR^{13}$, $-SO_2NH-C(R^{13}R^{13})-(Z)_g-R^{13}$, a cyclic sugar or oligosaccharide, a cyclic amino sugar or oligosaccharide,

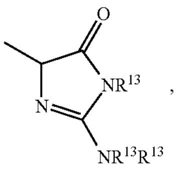

, or

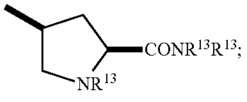

each Ar is, independently, phenyl, substituted phenyl, wherein the substituents of the substituted phenyl are 1-3 substituents independently selected from the group consisting of OH, $OCH_3$, $NR^{13}R^{13}$, Cl, F, and $CH_3$, or heteroaryl, each W is independently, thiazolidinedione, oxazolidinedione, heteroaryl-$C(=O)NR^{13}R^{13}$, —CN, $-O-C(=S)NR^{13}R^{13}$, $-Z_gR^{13}$, $-CR^{10}(Z_gR^{13})(Z_gR^{13})$, —C(=O)OAr, $-C(=O)NR^{13}$Ar, imidazoline, tetrazole, tetrazole amide, $-SO_2NHR^{13}$, $-SO_2NH-C(R^{13}R^{13})-(Z)_g-R^{13}$, a cyclic sugar or oligosaccharide, a cyclic amino sugar or oligosaccharide,

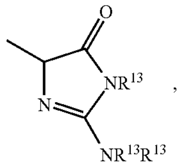

, or

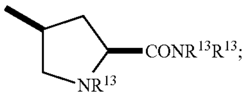

each $R^6$ is, independently, $-R^7$, $-OR^7$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, —O-glucuronide, —O-glucose,

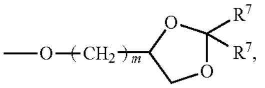

or

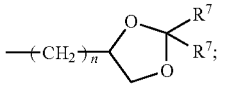

where when two $R^6$ are $-OR^{11}$ and are located adjacent to each other on a phenyl ring, the alkyl moieties of the two $R^6$ may be bonded together to form a methylenedioxy group; with the proviso that when at least two $-CH_2OR^8$ are located adjacent to each other, the $R^8$ groups may be joined to form a cyclic mono- or di-substituted 1,3-dioxane or 1,3-dioxolane, each $R^7$ is, independently, hydrogen lower alkyl, phenyl, substituted phenyl or $-CH_2(CHOR)^8{}_m-R^{10}$;

each $R^8$ is, independently, hydrogen, lower alkyl, $-C(=O)-R^{11}$, glucuronide, 2-tetrahydropyranyl, or

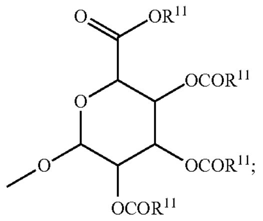

each $R^9$ is, independently, $-CO_2R^{13}$, $-CON(R^{13})_2$, $-SO_2CH_2R^{13}$, or $-C(=O)R^{13}$;

each $R^{10}$ is, independently, —H, $-SO_2CH_3$, $-CO_2R^{13}$, $-C(=O)NR^{13}R^{13}$, $-C(=O)R^{13}$, or $-(CH_2)_m-(CHOH)_n-CH_2OH$;

each Z is, independently, CHOH, C(=O), $-(CH_2)_n-$, $CHNR^{13}R^{13}$, $C=NR^{13}$, or $NR^{13}$;

each $R^{11}$ is, independently, lower alkyl;

each $R^{12}$ is independently, $-SO_2CH_3$, $-CO_2R^{13}$, $-C(=O)NR^{13}R^{13}$, $-C(=O)R^{13}$, or $-CH_2-(CHOH)_n-CH_2OH$;

each $R^{13}$ is, independently, hydrogen, $R^7$, $R^{10}$, $-(CH_2)_m-NR^{13}R^{13}$, $-(CH_2)_m-\overset{+}{N}R^{13}R^{13}R^{13}$, $-(CH_2)_m-(CHOR^8)_m-(CH_2)_mNR^{13}R^{13}$, $-(CH_2)_m-NR^{10}R^{10}$, -continued $$—(CH_2)_n—(CHOR^8)_m—(CH_2)_m\overset{+}{N}R^{13}R^{13}R^{13},$$

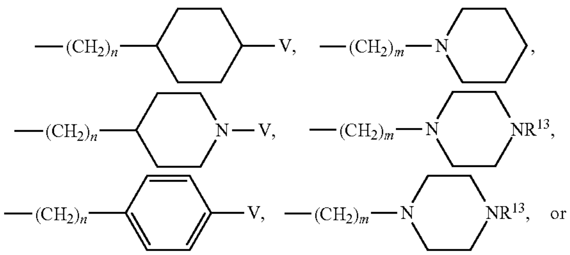

or

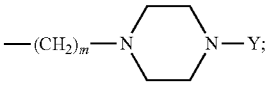

with the proviso that $NR^{13}R^{13}$ can be joined on itself to form a ring comprising one of the following:

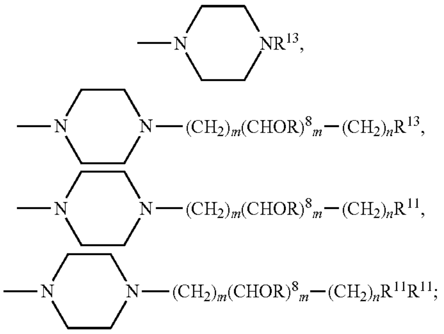

each Het is independently, $—NR^{13}$, —S—, —SO—, or $—SO_2—$; —O—, $—SO_2NR^{13}—$, $—NHSO_2—$, $—NR^{13}CO—$, or $—CONR^{13}—$;

each g is, independently, an integer from 1 to 6;

each m is, independently, an integer from 1 to 7;

each n is, independently, an integer from 0 to 7;

each Q is, independently, $C—R^5$, $C—R^6$, or a nitrogen atom, wherein at most three Q in a ring are nitrogen atoms;

each V is, independently, $$—(CH_2)_m—NR^7R^{13},\quad —(CH_2)_m—NR^7R^7,$$

$$—(CH_2)_m—\overset{+}{N}R^{11}R^{11}R^{11},$$

$$—(CH_2)_n—(CHOR^8)_m—(CH_2)_mNR^7R^{10},$$

$$—(CH_2)_n—NR^{10}R^{10},$$

$$—(CH_2)_n—(CHOR^8)_m—(CH_2)_mNR^7R^7,$$

$$—(CH_2)_n—(CHOR^8)_m—(CH_2)_m\overset{+}{N}R^{11}R^{11}R^{11},$$

with the proviso that when V is attached directly to a nitrogen atom, then V can also be, independently, $R^7$, $R^{10}$, or $(R^{11})_2$;

wherein for any of the above compounds when two $—CH_2OR^8$ groups are located 1,2- or 1,3- with respect to each other the $R^8$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all enantiomers, diastereomers, and racemic mixtures thereof.

The present invention also provides pharmaceutical compositions which contain a compound described above.

The present invention also provides a method of promoting hydration of mucosal surfaces, comprising:

administering an effective amount of a compound represented by formula (I) to a mucosal surface of a subject.

The present invention also provides a method of restoring mucosal defense, comprising:

topically administering an effective amount of compound represented by formula (I) to a mucosal surface of a subject in need thereof.

The present invention also provides a method of blocking ENaC, comprising:

contacting sodium channels with an effective amount of a compound represented by formula (I).

The present invention also provides a method of promoting mucus clearance in mucosal surfaces, comprising:

administering an effective amount of a compound represented by formula (I) to a mucosal surface of a subject.

The present invention also provides a method of treating chronic bronchitis, comprising:

administering an effective amount of a compound represented by formula (I) to a subject in need thereof.

The present invention also provides a method of treating cystic fibrosis, comprising:

administering an effective amount of compound represented by formula (I) to a subject in need thereof.

The present invention also provides a method of treating rhinosinusitis, comprising:

administering an effective amount of a compound represented by a formula (I) to a subject in need thereof.

The present invention also provides a method of treating nasal dehydration, comprising:

administering an effective amount of a compound represented by formula (I) to the nasal passages of a subject in need thereof.

In a specific embodiment, the nasal dehydration is brought on by administering dry oxygen to the subject.

The present invention also provides a method of treating sinusitis, comprising:

administering an effective amount of a compound represented by formula (I) to a subject in need thereof.

The present invention also provides a method of treating pneumonia, comprising:

administering an effective amount of a compound represented by formula (I) to a subject in need thereof.

The present invention also provides a method of preventing ventilator-induced pneumonia, comprising:

administering an effective compound represented by formula (I) to a subject by means of a ventilator.

The present invention also provides a method of treating asthma, comprising:

administering an effective amount of a compound represented by formula (I) to a subject in need thereof.

The present invention also provides a method of treating primary ciliary dyskinesia, comprising:

administering an effective amount of a compound represented by formula (I) to a subject in need thereof.

The present invention also provides a method of treating otitis media, comprising:

administering an effective amount of a compound represented by formula (I) to a subject in need thereof.

The present invention also provides a method of inducing sputum for diagnostic purposes, comprising:

administering an effective amount of compound represented by formula (I) to a subject in need thereof.

The present invention also provides a method of treating chronic obstructive pulmonary disease, comprising:

administering an effective amount of a compound represented by formula (I) to a subject in need thereof.

The present invention also provides a method of treating emphysema, comprising:

administering an effective amount of a compound represented by formula (I) to a subject in need thereof.

The present invention also provides a method of treating dry eye, comprising:

administering an effective amount of a compound represented by formula (I) to the eye of the subject in need thereof.

The present invention also provides a method of promoting ocular hydration, comprising:

administering an effective amount of a compound represented by formula (I) to the eye of the subject.

The present invention also provides a method of promoting corneal hydration, comprising:

administering an effective amount of a compound represented by formula (I) to the eye of the subject.

The present invention also provides a method of treating Sjögren's disease, comprising:

administering an effective amount of compound represented by formula (I) to a subject in need thereof.

The present invention also provides a method of treating vaginal dryness, comprising:

administering an effective amount of a compound represented by formula (I) to the vaginal tract of a subject in need thereof.

The present invention also provides a method of treating dry skin, comprising:

administering an effective amount of a compound represented by formula (I) to the skin of a subject in need thereof.

The present invention also provides a method of treating dry mouth (xerostomia), comprising:

administering an effective amount of compound represented by formula (I) to the mouth of the subject in need thereof.

The present invention also provides a method of treating distal intestinal obstruction syndrome, comprising:

administering an effective amount of compound represented by formula (I) to a subject in need thereof.

The present invention also provides a method of treating esophagitis, comprising:

administering an effective amount of a compound represented by formula (I) to a subject in need thereof.

The present invention also provides a method of treating constipation, comprising:

administering an effective amount of a compound represented by formula (I) to a subject in need thereof. In one embodiment of this method, the compound is administered either orally or via a suppository or enema.

The present invention also provides a method of treating chronic diverticulitis comprising:

administering an effective amount of a compound represented by formula (I) to a subject in need thereof.

The present invention also provides a method of treating hypertension, comprising administering the compound represented by formula (I) to a subject in need thereof.

The present invention also provides a method of reducing blood pressure, comprising administering the compound represented by formula (I) to a subject in need thereof.

The present invention also provides a method of treating edema, comprising administering the compound represented by formula (I) to a subject in need thereof.

The present invention also provides a method of promoting diuresis, comprising administering the compound represented by formula (I) to a subject in need thereof.

The present invention also provides a method of promoting natriuresis, comprising administering the compound represented by formula (I) to a subject in need thereof.

The present invention also provides a method of promoting saluresis, comprising administering the compound represented by formula (I) to a subject in need thereof.

DETAILED DESCRIPTION OF THE INVENTION

The present invention is based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels as compared to the parent administered compound, after they are absorbed from mucosal surfaces after administration. This important property means that the compounds will have a lower tendency to cause undesired side-effects by blocking sodium channels located at untargeted locations in the body of the recipient, e.g., in the kidneys.

The present invention is also based on the discovery that certain compounds embraced by formula (1) target the kidney and thus may be used as cardiovascular agents.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or —$N(R^2)_2$. The alkyl moiety of the lower alkoxy groups is the same as described above. Examples of mononuclear aryl include phenyl groups. The phenyl group may be unsubstituted or substituted as described above. The preferred identity of Y is —$N(R^2)_2$. Particularly preferred are such compounds where each $R^2$ is hydrogen.

$R^1$ may be hydrogen or lower alkyl. Hydrogen is preferred for $R^1$.

Each $R^2$ may be, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—C(═O)$NR^7R^{10}$, —$(CH_2)_n$—$Z_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

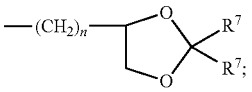

Hydrogen and lower alkyl, particularly $C_1$-$C_3$ alkyl are preferred for $R^2$. Hydrogen is particularly preferred.

$R^3$ and $R^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^3$ and $R^4$ is a group represented by formula (A).

Preferred compounds are those where one of $R^3$ and $R^4$ is hydrogen and the other is represented by formula (A).

In formula (A), the moiety —$(C(R^L)_2)_o$-x-$(C(R^L)_2)_p$— defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, C(═O), CHOH, C(═N—$R^{10}$), $CHNR^7R^{10}$, or represents a single bond;

Therefore, when x represents a single bond, the alkylene chain bonded to the ring is represented by the formula —$(C(R^L)_2)_{o+p}$—, in which the sum o+p is from 1 to 10.

Each $R^L$ may be, independently, —$R^7$, —$(CH_2)_n$—$OR^8$, —O—$(CH_2)_m$, —$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(═O)$NR^7R^{10}$, —O—$(CH_2)_m$—C(═O)$NR^7R^{10}$, —$(CH_2)_n$-$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

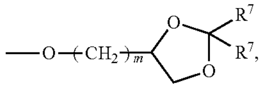 or 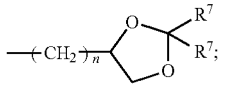

The preferred $R^L$ groups include —H, —OH, —$N(R^7)_2$, especially where each $R^7$ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula —$CHR^L$—. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula $$—(CH_2)_o\text{-}x\text{-}(CH_2)_p—.$$

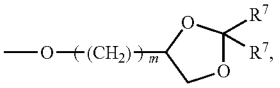 or 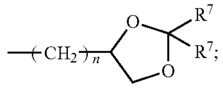

Each $R^5$ is, independently, Link-$(CH_2)_n$—CAP, Link-$(CH_2)_n(CHOR^8)(CHOR^8)_n$—CAP, Link-$(CH_2CH_2O)_m$—$CH_2$—CAP, Link-$(CH_2CH_2O)_m$—$CH_2CH_2$—CAP, Link-$(CH_2)_n$—$(Z)_g$—CAP, Link-$(CH_2)_n(Z)_g$—$(CH_2)_m$—CAP, Link-$(CH_2)_n$—$NR^{13}$—$CH_2(CHOR^8)(CHOR^8)$, —CAP, Link-$(CH_2)_n$—$(CHOR^8)_mCH_2$—$NR^{13}$—$(Z)_g$—CAP, Link-$(CH_2)_nNR^{13}$—$(CH_2)_m(CHOR^8)_nCH_2NR^{13}$—$(Z)_g$—CAP, Link-$(CH_2)_m$—$(Z)_g$—$(CH_2)_m$—CAP, Link-NH—C(═O)—NH—$(CH_2)_m$—CAP, Link-$(CH_2)_m$—C(═O)$NR^{13}$—$(CH_2)_m$ —C(═O)$NR^{10}R^{10}$, Link-$(CH_2)_m$—C(═O)$NR^{13}$—$(CH_2)_m$—CAP, Link-$(CH_2)_m$—C(═O)$NR^{11}R^{11}$, Link-$(CH_2)_m$—C(═O)$NR^{12}R^{12}$, Link-$(CH_2)_n$—$(Z)_g$—$(CH_2)_m$—$(Z)_g$—CAP, Link-$Z_g$—$(CH_2)_m$-Het-$(CH_2)_m$—CAP.

Each Link is, independently, —O—, $(CH_2)_n$—, —$O(CH_2)_m$—, —$NR^{13}$—C(═O)—$NR^{13}$, —$NR^{13}$—C(═O)—$(CH_2)_m$—, —C(═O)$NR^{13}$—$(CH_2)_m$, —$(CH_2)_n$—$Z_g$—$(CH_2)_n$, —S—, —SO—, —$SO_2$—, $SO_2NR^7$—, $SO_2NR^{10}$—, or -Het-.

each CAP is, independently, thiazolidinedione, oxazolidinedione, heteroaryl-C(═O)N $R^{13}R^{13}$, heteroaryl-W, —CN, —O—C(═S)$NR^{13}R^{13}$, —$Z_gR^{13}$, —$CR^{10}(Z_gR^{13})(Z_gR^{13})$, —C(═O)$NR^{13}$Ar, imidazoline, tetrazole, tetrazole amide, —$SO_2NHR^{13}$, —$SO_2NH$—$C(R^{13}R^{13})$-$(Z)_g$—$R^{13}$, a cyclic sugar or oligosaccharide, a cyclic amino sugar or oligosaccharide,

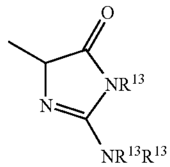 , or 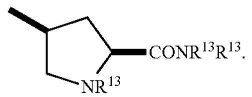

Each Ar is, independently, phenyl, substituted phenyl, wherein the substituents of the substituted phenyl are 1-3 substituents independently selected from the group consisting of OH, $OCH_3$, $NR^{13}R^{13}$, Cl, F, and $CH_3$, or heteroaryl.

Each W is independently, thiazolidinedione, oxazolidinedione, heteroaryl-C(═O)$NR^{13}R^{13}$, —CN, —O—C(═S)$NR^{13}R^{13}$, —$Z_gR^{13}$, —$CR^{10}(Z_gR^{13})(Z_gR^{13})$, —C(═O)OAr, —C(═O)$NR^{13}$Ar, imidazoline, tetrazole, tetrazole amide, —$SO_2NHR^{13}$, —$SO_2NH$—$C(R^{13}R^{13})$—$(Z)_g$—$R^{13}$, a cyclic sugar or oligosaccharide, a cyclic amino sugar or oligosaccharide,

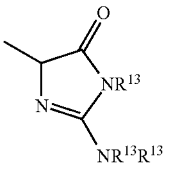

, or

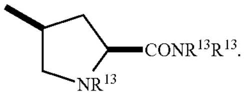

Examples of heteroaryl include pyridyl, pyrazyl, tinazyl, furyl, furfuryl, thienyl, tetrazyl, thiazolidinedionyl and imidazoyl, pyrrolyl, furanyl, thiophenyl, quinolyl, indolyl, adenyl, pyrazolyl, thiazolyl, isoxazolyl, indolyl, benzimidazolyl, purinyl, quinolinyl, isoquinolinyl, pyridazyl, pyrimidyl, pyrazyl, 1,2,3-triazyl, 1,2,4-triazyl, 1,3,5-triazyl, cinnolyl, phthalazyl, quinazolyl, quinoxalyl or pterdyl groups.

Each $R^6$ is, independently, $—R^7$, $—OR^7$, $—OR^{11}$, $—N(R^7)_2$, $—(CH_2)_m—OR^8$, $—O—(CH_2)_m—OR^8$, $—(CH_2)_n—NR^7R^{10}$, $—O—(CH_2)_m—NR^7R^{10}$, $—(CH_2)_n(CHOR^8)(CHOR^8)_n—CH_2OR^8$, $—O—(CH_2)_m(CHOR^8)(CHOR^8)_n—CH_2OR^8$, $—(CH_2CH_2O)_m—R^8$, $—O—(CH_2CH_2O)_m—R^8$, $—(CH_2CH_2O)_m—CH_2CH_2NR^7R^{10}$, $—O—(CH_2CH_2O)_m—CH_2CH_2NR^7R^{10}$, $—(CH_2)_n—C(=O)NR^7R^{10}$, $—O—(CH_2)_m—C(=O)NR^7R^{10}$, $—(CH_2)_n—(Z)_g—R^7$, $—O—(CH_2)_m—(Z)_g—R^7$, $—(CH_2)_n—NR^{10}—CH_2(CHOR^8)(CHOR^8)_n—CH_2OR^8$, $—O—(CH_2)_m—NR^{10}—CH_2(CHOR^8)(CHOR^8)_n—CH_2OR^8$, $—(CH_2)_n—CO_2R^7$, $—O—(CH_2)_m—CO_2R^7$, $—OSO_3H$, —O-glucuronide, —O-glucose,

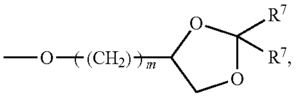

or

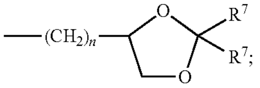

where when two $R^6$ are $—OR^{11}$ and are located adjacent to each other on a phenyl ring, the alkyl moieties of the two $R^6$ may be bonded together to form a methylenedioxy group;

with the proviso that when at least two $—CH_2OR^8$ are located adjacent to each other, the $R^8$ groups may be joined to form a cyclic mono- or di-substituted 1,3-dioxane or 1,3-dioxolane.

In addition, one of more of the $R^6$ groups can be one of the $R^5$ groups which fall within the broad definition of $R^6$ set forth above.

When two $R^6$ are $—OR^{11}$ and are located adjacent to each other on a phenyl ring, the alkyl moieties of the two $R^6$ groups may be bonded together to form a methylenedioxy group, i.e., a group of the formula $—O—C_{1-12}—O—$.

As discussed above, $R^6$ may be hydrogen. Therefore, 1, 2, 3, or 4 $R^6$ groups may be other than hydrogen. Preferably at most 3 of the $R^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Q in formula (A) is $C—R^5$, $C—R^6$, or a nitrogen atom, where at most three Q in a ring are nitrogen atoms. Thus, there may be 1, 2, or 3 nitrogen atoms in a ring. Preferably, at most two Q are nitrogen atoms. More preferably, at most one Q is a nitrogen atom. In one particular embodiment, the nitrogen atom is at the 3-position of the ring. In another embodiment of the invention, each Q is either $C—R^5$ or $C—R^6$, i.e., there are no nitrogen atoms in the ring.

More specific examples of suitable groups represented by formula (A) are shown in formulas (B)-(E) below:

(B)

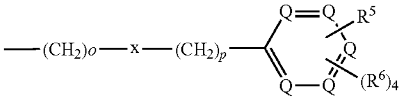

where o, x, p, $R^5$, and $R^6$, are as defined above;

(C)

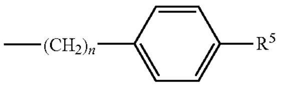

where n is an integer from 1 to 10 and $R^5$ is as defined above;

(D)

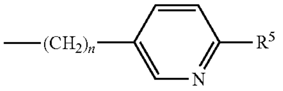

where n is an integer from 1 from 10 and $R^5$ is as defined above;

(E)

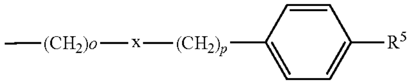

where o, x, p, and $R^5$ are as defined above.

In a preferred embodiment of the invention, Y is $—NH_2$.

In another preferred embodiment, $R^2$ is hydrogen.

In another preferred embodiment, $R^1$ is hydrogen.

In another preferred embodiment, X is chlorine.

In another preferred embodiment, $R^3$ is hydrogen.

In another preferred embodiment, $R^L$ is hydrogen.

In another preferred embodiment, o is 4.

In another preferred embodiment, p is 0.

In another preferred embodiment, the sum of o and p is 4.

In another preferred embodiment, x represents a single bond.

In another preferred embodiment, $R^6$ is hydrogen.

In another preferred embodiment, at most one Q is a nitrogen atom.

In another preferred embodiment, no Q is a nitrogen atom.

In a preferred embodiment of the present invention:

X is halogen;

Y is $—N(R^7)_2$;

$R^1$ is hydrogen or $C_1$-$C_3$ alkyl;

$R^2$ is $—R^7$, $—OR^7$, $CH_2OR^7$, or $—CO_2R^7$;

$R^3$ is a group represented by formula (A); and $R^4$ is hydrogen, a group represented by formula (A), or lower alkyl;

In another preferred embodiment of the present invention:

X is chloro or bromo;

Y is $—N(R^7)_2$;

$R^2$ is hydrogen or $C_1$-$C_3$ alkyl;

at most three $R^6$ are other than hydrogen as described above;

at most three $R^L$ are other than hydrogen as described above; and at most 2 Q are nitrogen atoms.

In another preferred embodiment of the present invention:

Y is $—NH_2$;

In another preferred embodiment of the present invention:

$R^4$ is hydrogen;

at most one $R^L$ is other than hydrogen as described above;

at most two $R^6$ are other than hydrogen as described above; and at most 1 Q is a nitrogen atom.

In another preferred embodiment of the present invention the compound of formula (1) is represented by the formula:

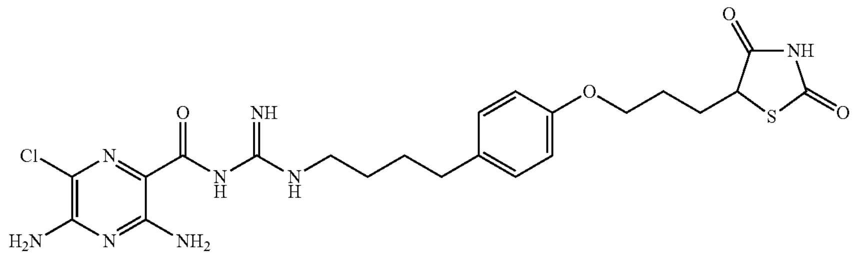

In another preferred embodiment of the present invention the compound of formula (1) is represented by the formula:

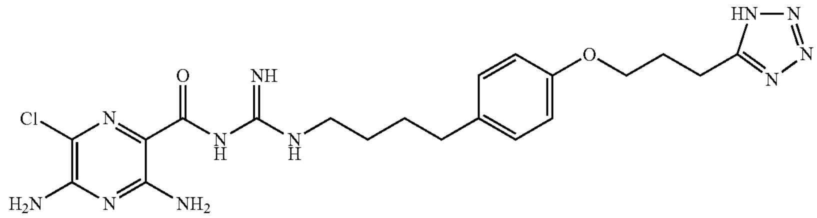 [SMILES: N=C(NCCCCc1ccc(OCCCc2nnn[nH]2)cc1)NC(=O)c1nc(Cl)c(N)nc1N]

In another preferred embodiment of the present invention the compound of formula (1) is represented by the formula:

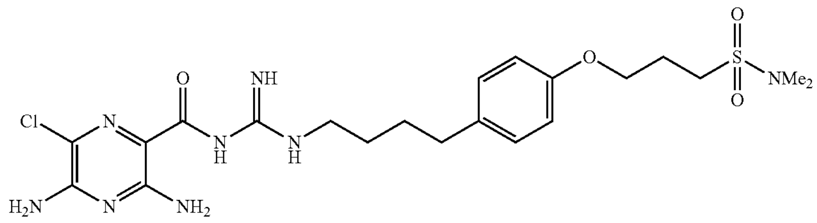 [SMILES: CN(C)S(=O)(=O)CCCOc1ccc(CCCCNC(=N)NC(=O)c2nc(Cl)c(N)nc2N)cc1]

In another preferred embodiment of the present invention the compound of formula (1) is represented by the formula:

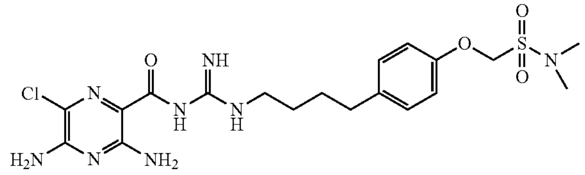 [SMILES: CN(C)S(=O)(=O)COc1ccc(CCCCNC(=N)NC(=O)c2nc(Cl)c(N)nc2N)cc1]

In another preferred embodiment of the present invention the compound of formula (1) is represented by the formula:

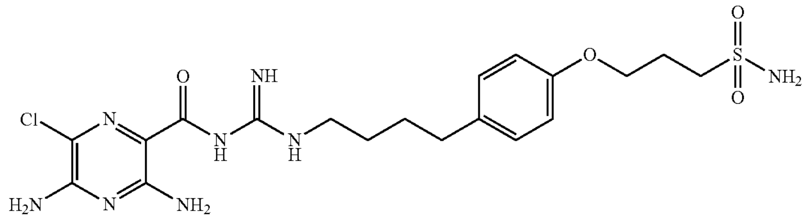 [SMILES: N=C(NCCCCc1ccc(OCCCS(N)(=O)=O)cc1)NC(=O)c1nc(Cl)c(N)nc1N]

In another preferred embodiment of the present invention the compound of formula (1) is represented by the formula:

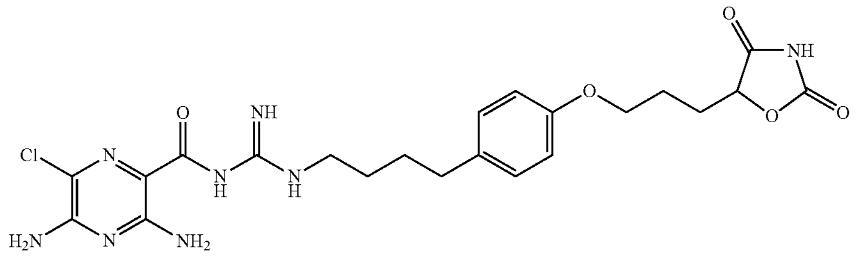 [SMILES: N=C(NCCCCc1ccc(OCCCC2OC(=O)NC2=O)cc1)NC(=O)c1nc(Cl)c(N)nc1N]

In another preferred embodiment of the present invention the compound of formula (1) is represented by the formula:

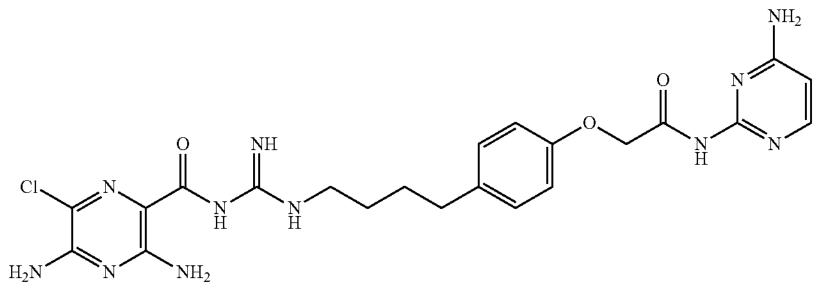 [SMILES: N=C(NCCCCc1ccc(OCC(=O)Nc2nccc(N)n2)cc1)NC(=O)c1nc(Cl)c(N)nc1N]

In another preferred embodiment of the present invention the compound of formula (1) is represented by the formula:

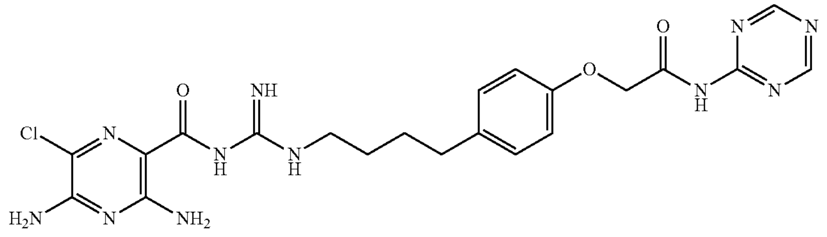 [SMILES: N=C(NCCCCc1ccc(OCC(=O)Nc2ncncn2)cc1)NC(=O)c1nc(Cl)c(N)nc1N]

In another preferred embodiment of the present invention the compound of formula (1) is represented by the formula:

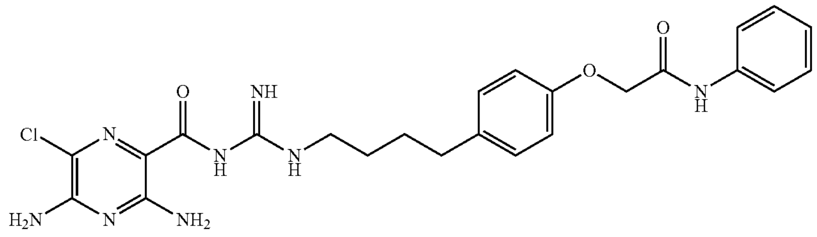 [SMILES: N=C(NCCCCc1ccc(OCC(=O)Nc2ccccc2)cc1)NC(=O)c1nc(Cl)c(N)nc1N]

In another preferred embodiment of the present invention the compound of formula (1) is represented by the formula:

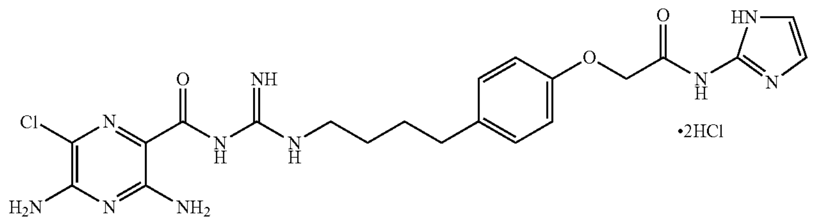 [SMILES: N=C(NCCCCc1ccc(OCC(=O)Nc2ncc[nH]2)cc1)NC(=O)c1nc(Cl)c(N)nc1N]

In another preferred embodiment of the present invention the compound of formula (1) is represented by the formula:

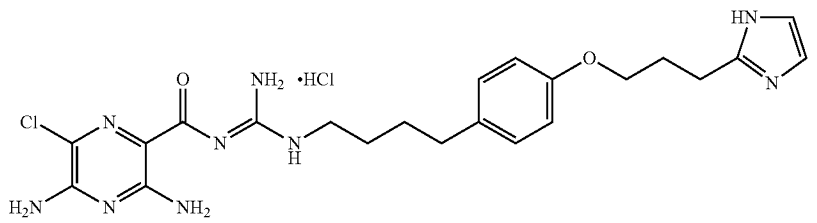 [SMILES: N/C(=N\C(=O)c1nc(Cl)c(N)nc1N)NCCCCc1ccc(OCCCc2ncc[nH]2)cc1 ; Cl]

In another preferred embodiment of the present invention the compound of formula (1) is represented by the formula:

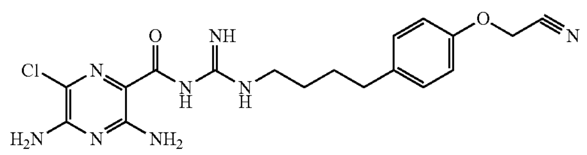 [SMILES: N#CCOc1ccc(CCCCNC(=N)NC(=O)c2nc(Cl)c(N)nc2N)cc1]

In another preferred embodiment of the present invention the compound of formula (1) is represented by the formula:

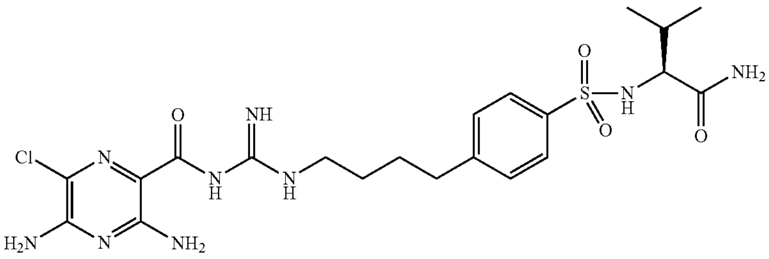 [SMILES: CC(C)[C@H](NS(=O)(=O)c1ccc(CCCCNC(=N)NC(=O)c2nc(Cl)c(N)nc2N)cc1)C(N)=O]
In another preferred embodiment of the present invention the compound of formula (1) is represented by the formula:
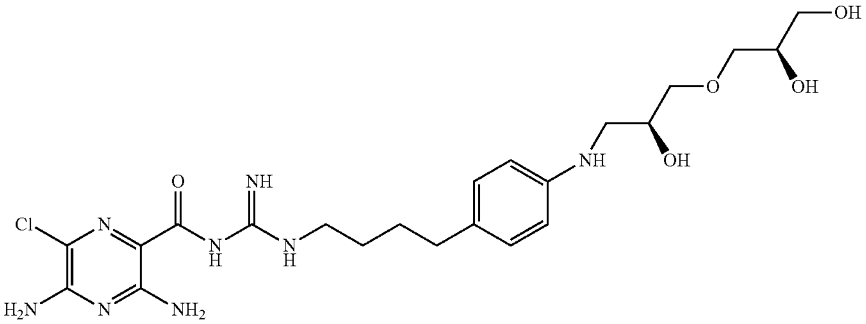 [SMILES: N=C(NCCCCc1ccc(NC[C@H](O)COC[C@H](O)CO)cc1)NC(=O)c1nc(Cl)c(N)nc1N]
In another preferred embodiment of the present invention the compound of formula (1) is represented by the formula:
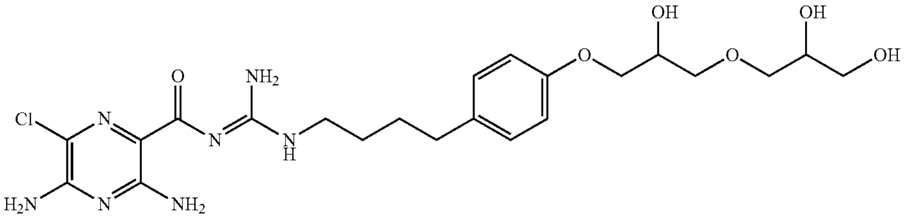 [SMILES: N/C(=N\C(=O)c1nc(Cl)c(N)nc1N)NCCCCc1ccc(OCC(O)COCC(O)CO)cc1]
In another preferred embodiment of the present invention the compound of formula (1) is represented by the formula:
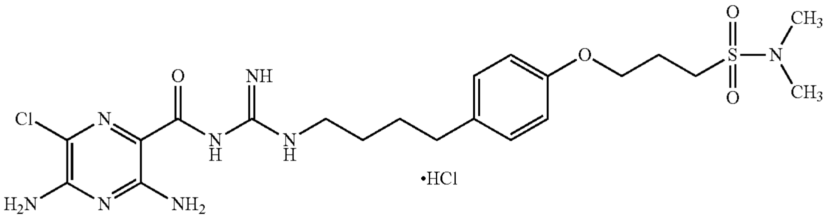 [SMILES: CN(C)S(=O)(=O)CCCOc1ccc(CCCCNC(=N)NC(=O)c2nc(Cl)c(N)nc2N)cc1 ; Cl]

In another preferred embodiment of the present invention the compound of formula (1) is represented by the formula:

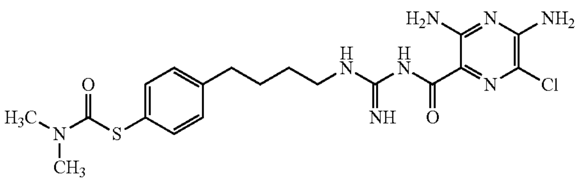 [SMILES: CN(C)C(=O)Sc1ccc(CCCCNC(=N)NC(=O)c2nc(Cl)c(N)nc2N)cc1]

In another preferred embodiment of the present invention the compound of formula (1) is represented by the formula:

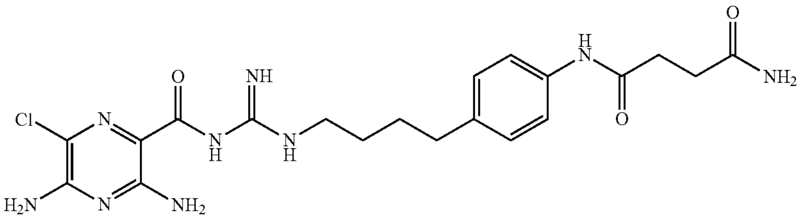 [SMILES: N=C(NCCCCc1ccc(NC(=O)CCC(N)=O)cc1)NC(=O)c1nc(Cl)c(N)nc1N]

In another preferred embodiment of the present invention the compound of formula (1) is represented by the formula:

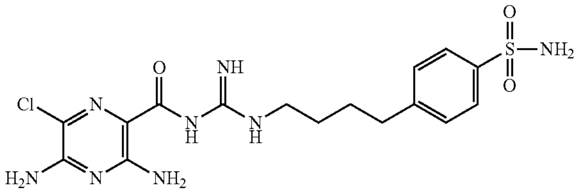 [SMILES: N=C(NCCCCc1ccc(S(N)(=O)=O)cc1)NC(=O)c1nc(Cl)c(N)nc1N]

In another preferred embodiment of the present invention the compound of formula (1) is represented by the formula:

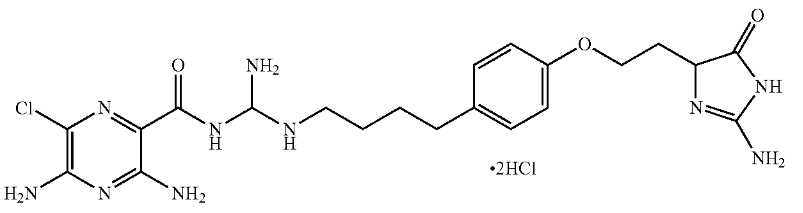 [SMILES: NC1=NC(CCOc2ccc(CCCCNC(N)NC(=O)c3nc(Cl)c(N)nc3N)cc2)C(=O)N1]

In another preferred embodiment of the present invention the compound of formula (1) is represented by the formula:

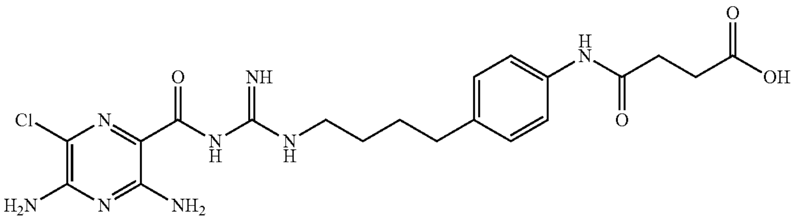 [SMILES: N=C(NCCCCc1ccc(NC(=O)CCC(=O)O)cc1)NC(=O)c1nc(Cl)c(N)nc1N]

In another preferred embodiment of the present invention the compound of formula (1) is represented by the formula:

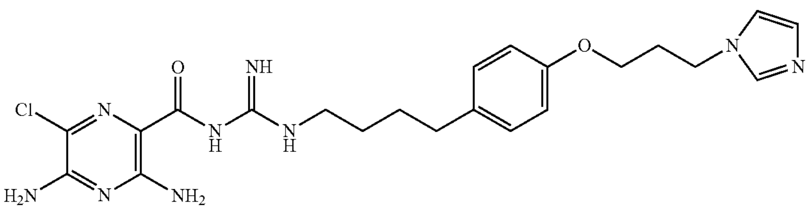 [SMILES: N=C(NCCCCc1ccc(OCCCn2ccnc2)cc1)NC(=O)c1nc(Cl)c(N)nc1N]

In another preferred embodiment of the present invention the compound of formula (1) is represented by the formula:

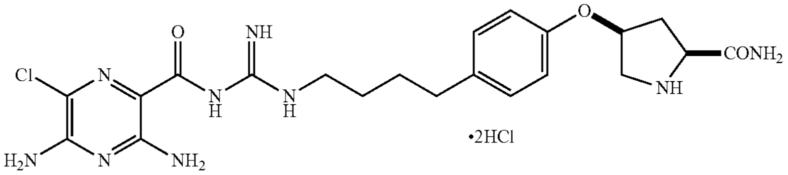

In another preferred embodiment of the present invention the compound of formula (1) is represented by the formula:

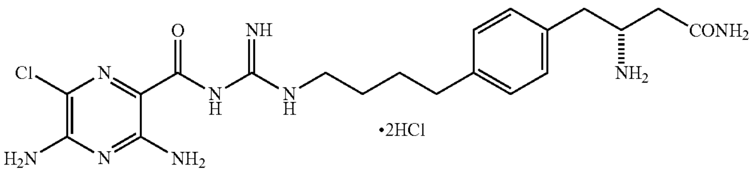 [SMILES: N=C(NCCCCc1ccc(C[C@@H](N)CC(N)=O)cc1)NC(=O)c1nc(Cl)c(N)nc1N]

In another preferred embodiment of the present invention the compound of formula (1) is represented by the formula:

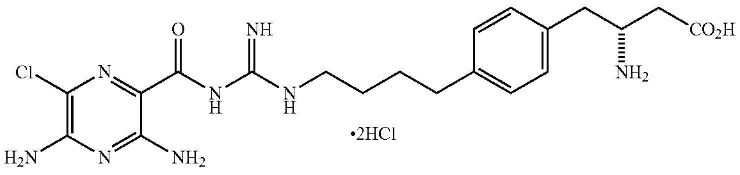 [SMILES: N=C(NCCCCc1ccc(C[C@@H](N)CC(=O)O)cc1)NC(=O)c1nc(Cl)c(N)nc1N]

The compounds of formula (I) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formula (I) are embraced by the present invention. All mixtures of such enantiomers and diastereomers are within the scope of the present invention.

Without being limited to any particular theory, it is believed that the compounds of formula (I) function in vivo as sodium channel blockers. By blocking epithelial sodium channels present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., *staphylococcus* infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genito-urethral surfaces, ocular surfaces or surfaces of the eye, the inner ear and the middle ear. For example, the active compounds of the present invention may be administered by any suitable means, including locally/topically, orally, or rectally, in an effective amount.

The compounds of the present invention are also useful for treating a variety of functions relating to the cardiovascular system. Thus, the compounds of the present invention are useful for use as antihypertensive agents. The compounds may also be used to reduce blood pressure and to treat edema. In addition, the compounds of the present invention are also useful for promoting diuresis, natriuresis, and saluresis. The compounds may be used alone or in combination with beta blockers, ACE inhibitors, HMGCoA reductase inhibitors, calcium channel blockers and other cardiovascular agents to treat hypertension, congestive heart failure and reduce cardiovascular mortality.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656,256, and U.S. Pat. No. 5,292,498, each of which is incorporated herein by reference.

Bronchodilators can also be used in combination with compounds of the present invention. These bronchodilators include, but are not limited to, β-adrenergic agonists including but not limited to epinephrine, isoproterenol, fenoterol, albutereol, terbutalin, pirbuterol, bitolterol, metaproterenol, iosetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein. Additional procedures useful for the preparation are found in USUSUS especially for the preparation of various Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 μm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by a suitable means know in the art, such as by nose drops, mists, etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^{4}$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 ($19^{th}$ ed. 1995), incorporated herein by reference. Pharmaceutical formulations suitable for nasal administration may be prepared as described in U.S. Pat. Nos. 4,389,393 to Schor; 5,707,644 to Illum; 4,294,829 to Suzuki; and 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below:

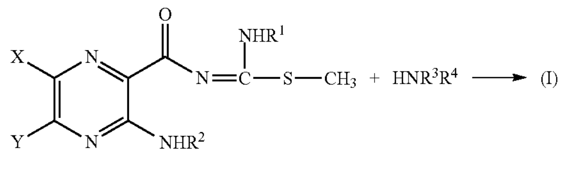

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Other methods useful for the preparation of these compounds, especially for the preparation of the novel HNR3R4 fragment are described in, for example, 229929US, 233377US, and 234105US, incorporated herein by reference. Schemes 1 to 11 are representative, but limited to, of procedures used to prepare the Sodium Channel Blockers described herein.

Scheme 1. Synthesis of PSA 17926
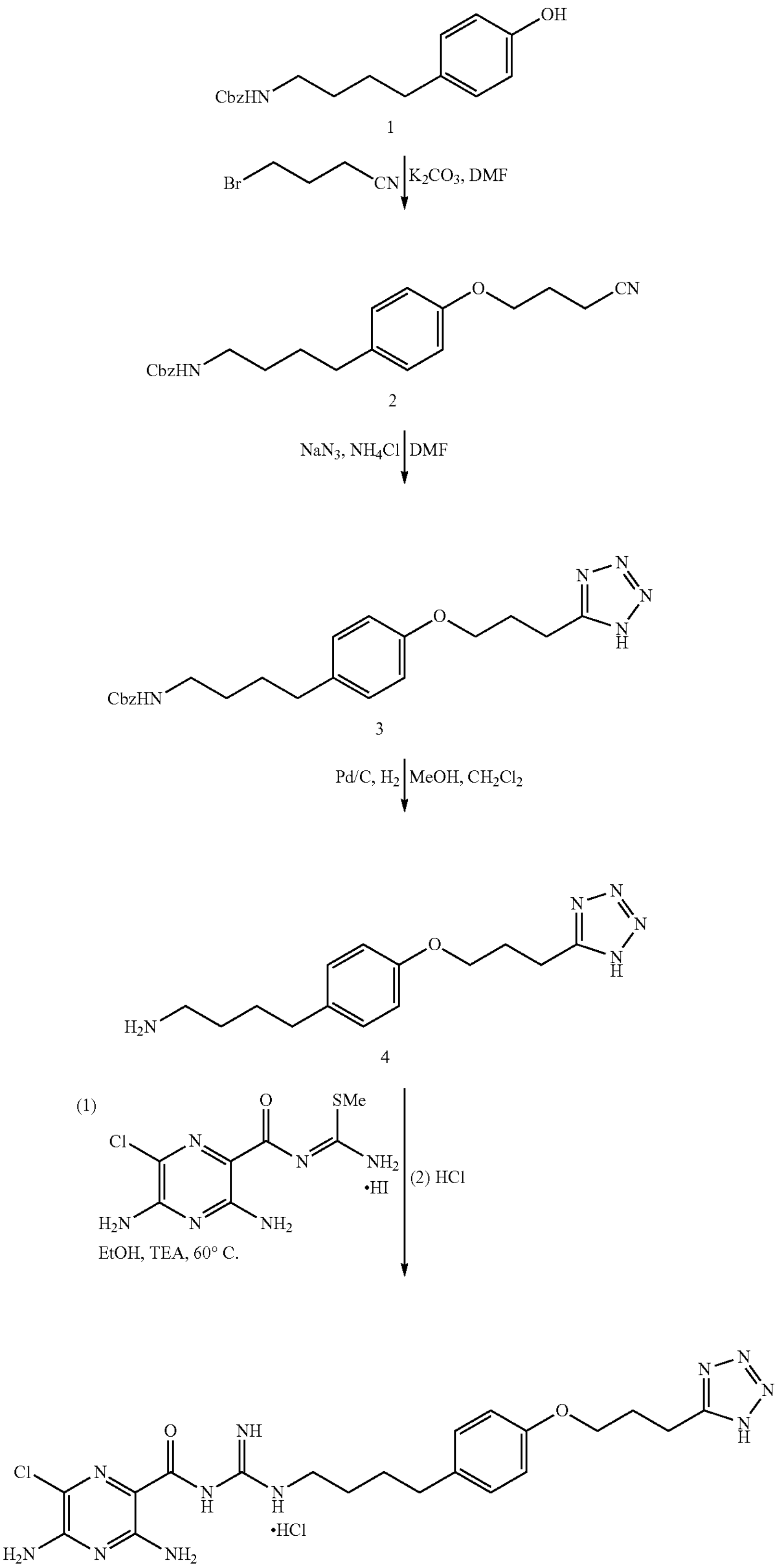
5, PSA 17926

Scheme 2. Synthesis of PSA 17846
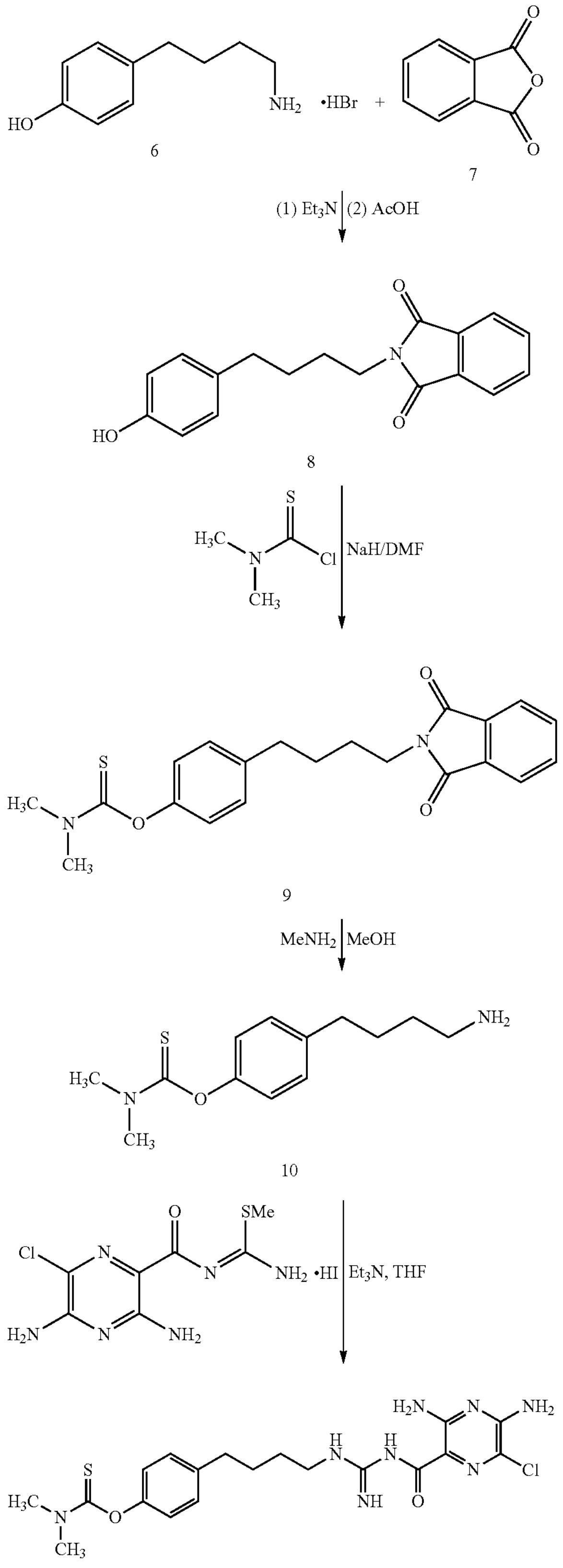
6
7
8
9
10
11, PSA 17846
Scheme 3. Synthesis of PSA 19008
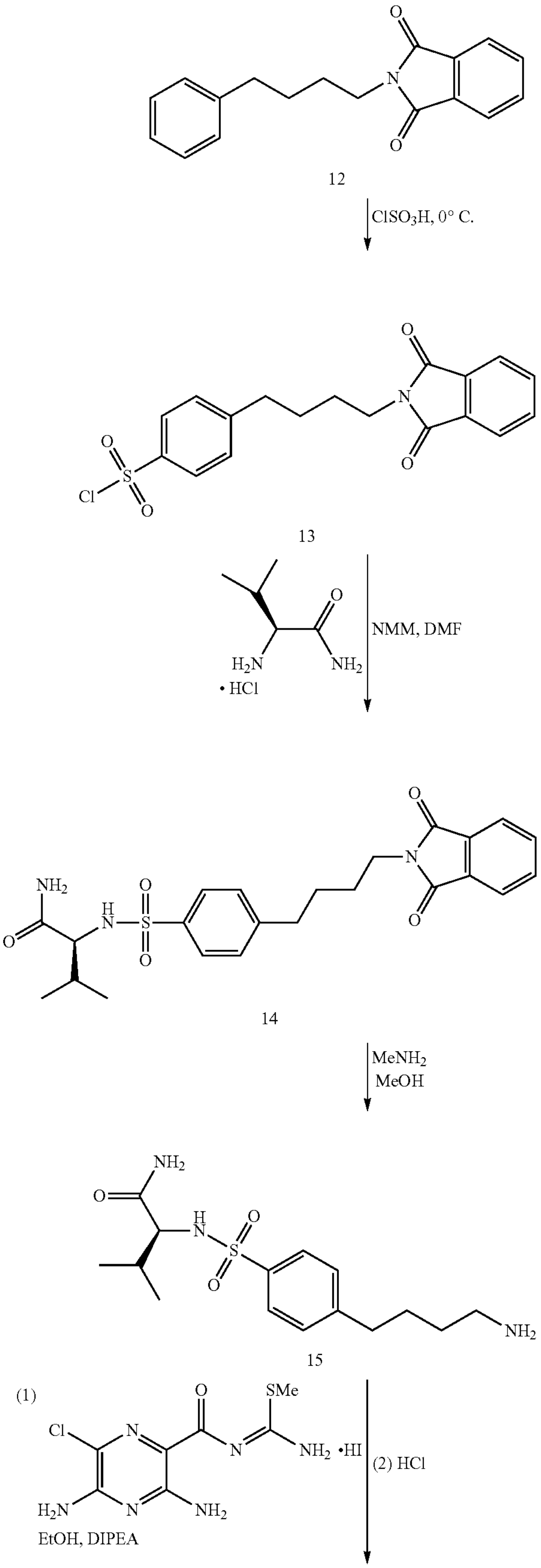
12
13
14
15

-continued
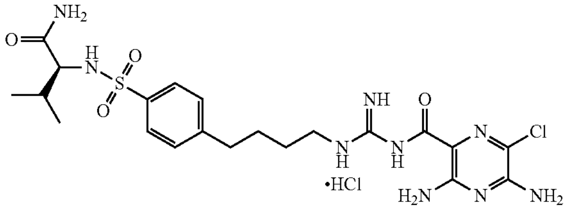
16, PSA 19008
Scheme 4. Synthesis of PSA 17482
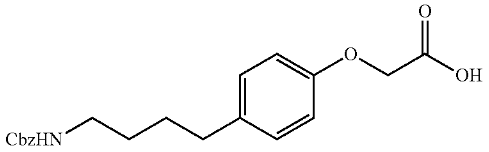
17
Aniline, EDCl | DMAP/$CH_2Cl_2$
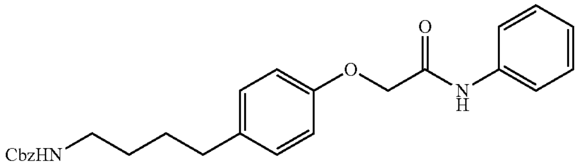
18
Pd/C, $H_2$
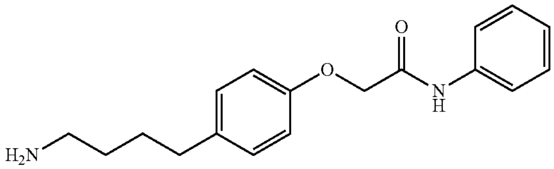
19
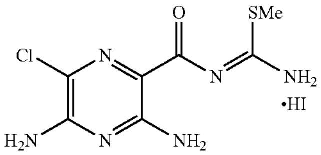
EtOH/DIPEA
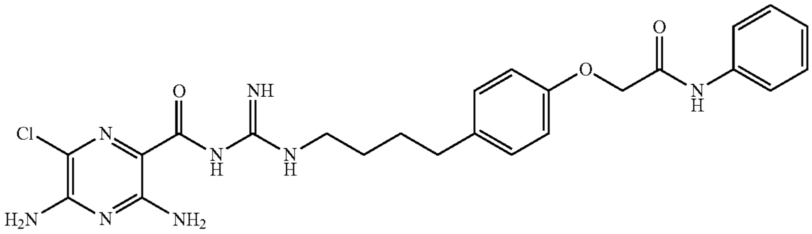
20, PSA 17482

Scheme 5. Synthesis of PSA 23022
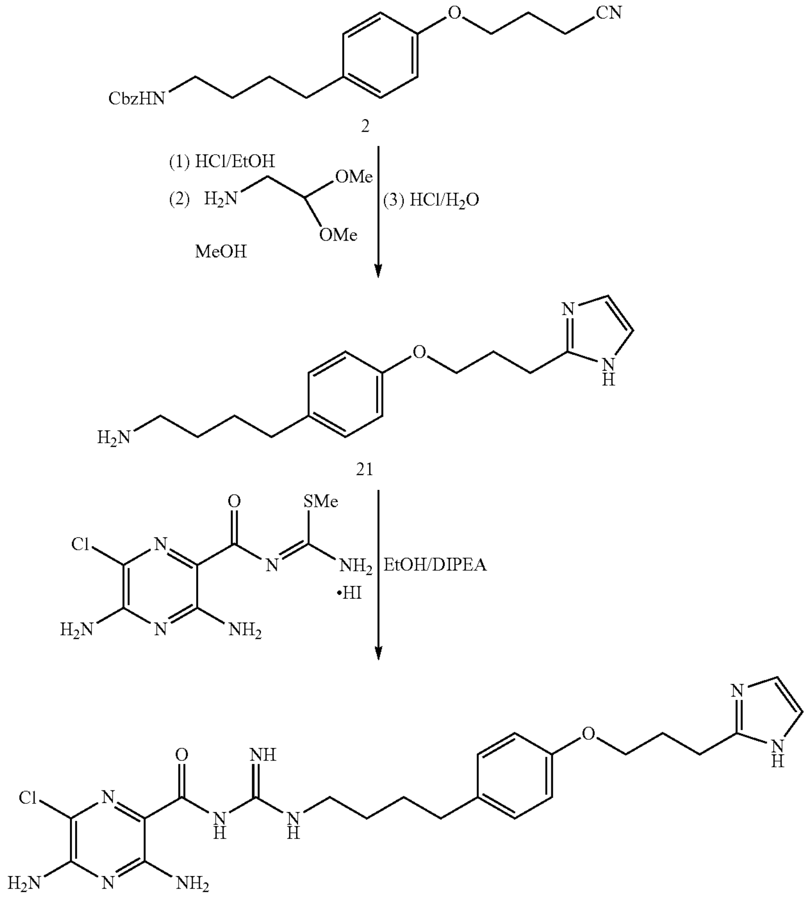
2
21
22, PSA 23022
Scheme 6. Synthesis of PSA 16826
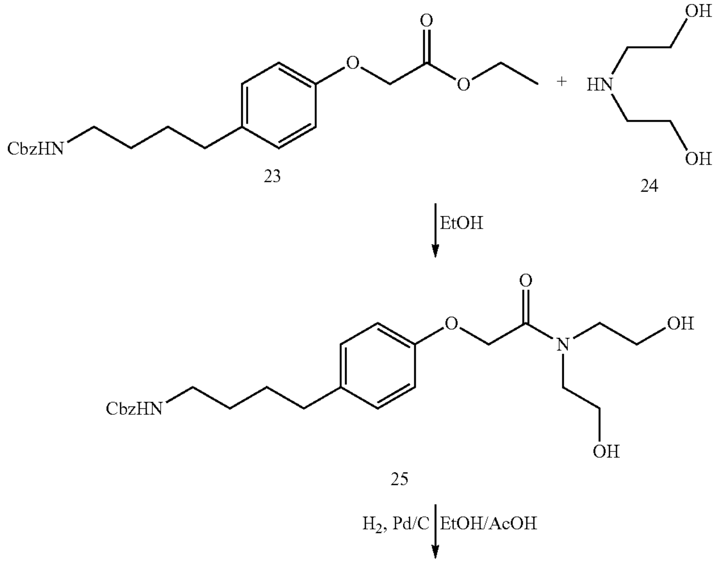
23
24
25

-continued
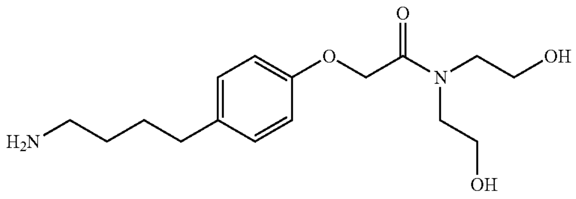
26
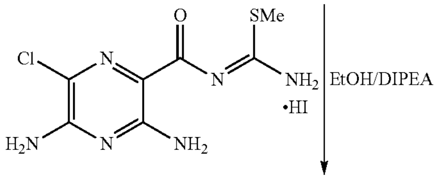
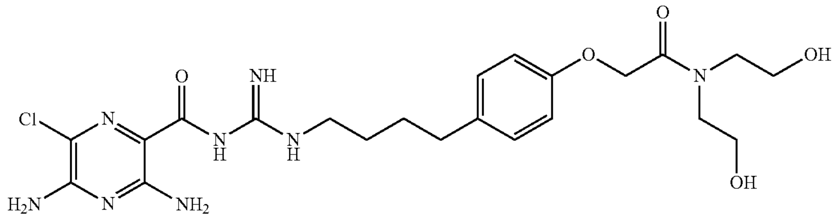
27, PSA 16826
Scheme 7. Synthesis of PSA 16313
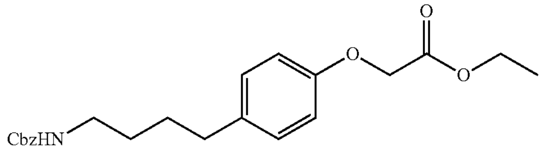
23
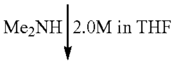
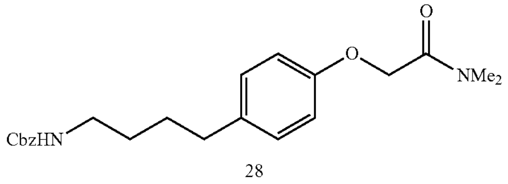
28
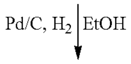
-continued
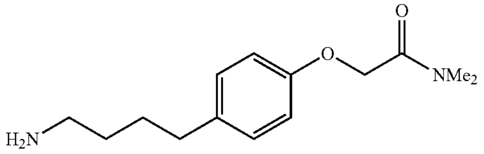
29
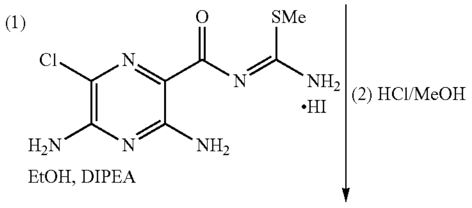
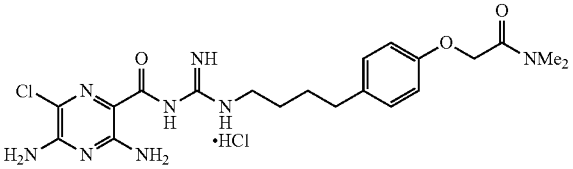
30, PSA 16313

Scheme 8. Synthesis of PSA 16437
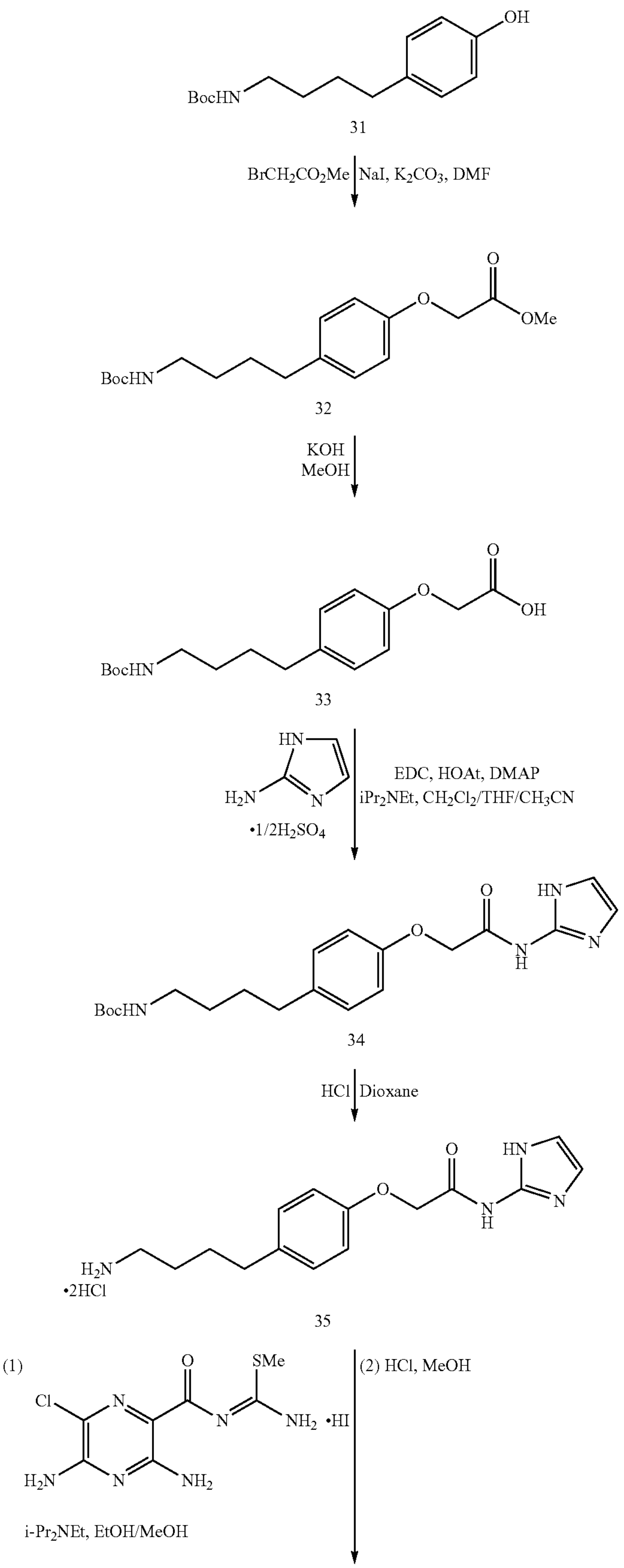

-continued
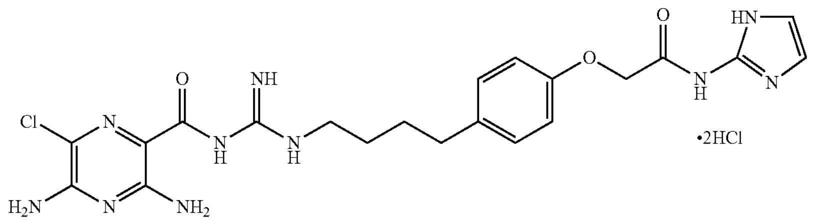
36, PSA 16437
Scheme 9. Synthesis of PSA 16314
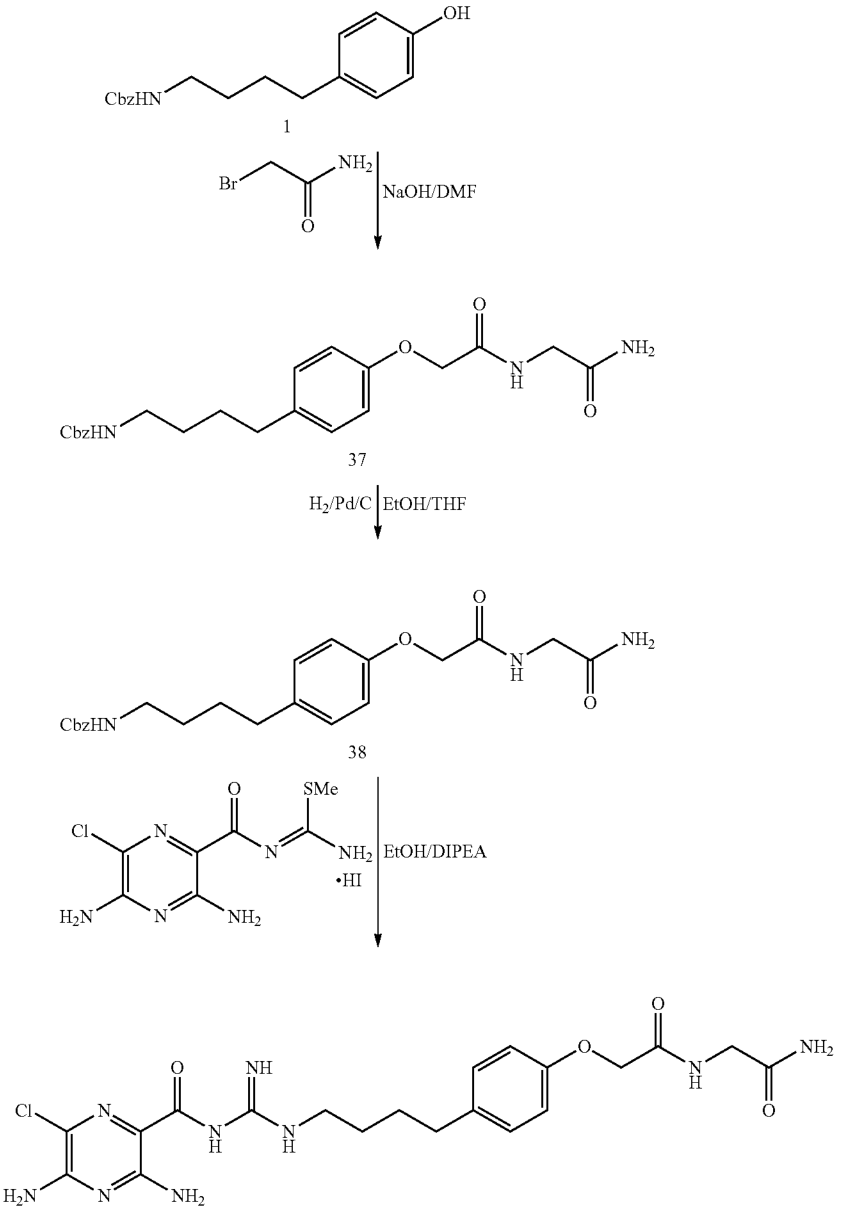
39, PSA 16314

Scheme 10. Synthesis of PSA 16208
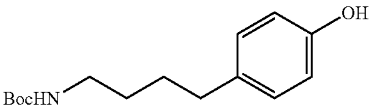
31
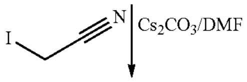
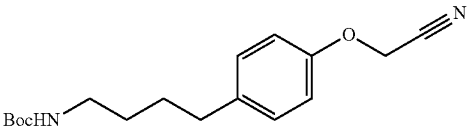
40
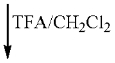
-continued
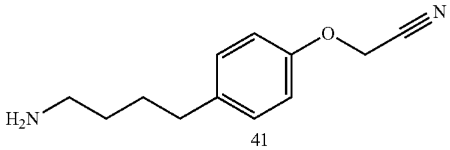
41
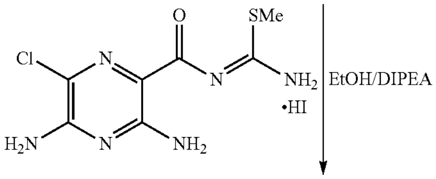
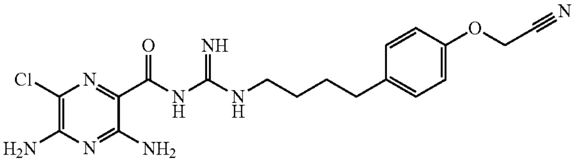
42, PSA 16208
Scheme 11. Synthesis of PSA 15143
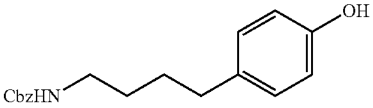
1
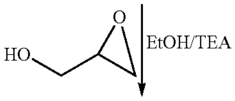
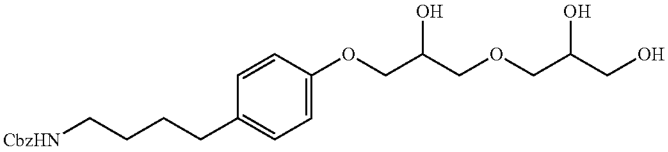
43
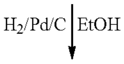
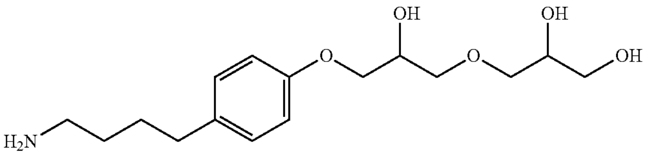
44
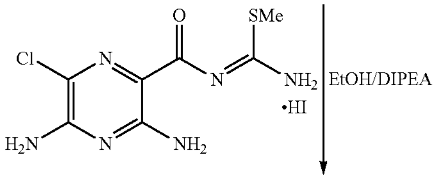

-continued

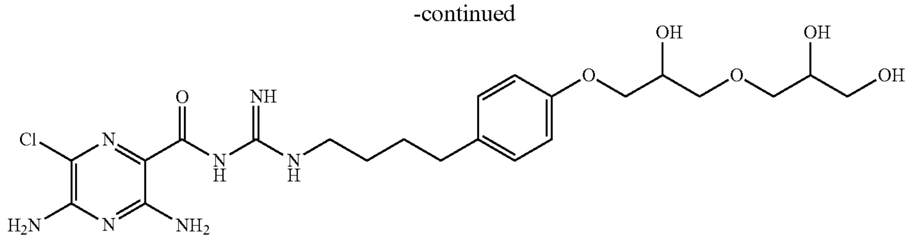

45, PSA 15143

Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1\times10^{-11}$ M to $3\times10^{-5}$M), and the cumulative change in $I_{SC}$ (inhibition) recorded. All drugs are prepared in dimethyl sulfoxide as stock solutions at a concentration of $1\times10^{-2}$ M and stored at −20° C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls.

Pharmacological Assays of Absorption (1) Apical Disappearance Assay

Bronchial cells (dog, human, sheep, or rodent cells) are seeded at a density of $0.25\times10^6$/cm$^2$ on a porous Transwell-Col collagen-coated membrane with a growth area of 1.13 cm$^2$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_t$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 μl) and is initiated by adding experimental sodium channel blockers or positive controls (amiloride, benzamil, phenamil) to the apical surface at an initial concentration of 10 μM. A series of samples (5 μl volume per sample) is collected at various time points, including 0, 5, 20, 40, 90 and 240 minutes. Concentrations are determined by measuring intrinsic fluorescence of each sodium channel blocker using a Fluorocount Microplate Fluorometer or HPLC. Quantitative analysis employs a standard curve generated from authentic reference standard materials of known concentration and purity. Data analysis of the rate of disappearance is performed using nonlinear regression, one phase exponential decay (Prism V 3.0).

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

3. In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 μl KBR, containing 10 μM test compound) is placed on the epithelial lumenal surface. Sequential 5 to 10 μl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolites, and HPLC mobilities of novel metabolites are then performed.

4. Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. All reagents and solvents were purchased from Aldrich Chemical Corp. and used without further purification. NMR spectra were obtained on either a Bruker WM 360 ($^1$H NMR at 360 MHz and $^{13}$C NMR at 90 MHz) or a Bruker AC 300 ($^1$H NMR at 300 MHz and $^{13}$C NMR at 75 MHz). Flash chromatography was performed on a Flash Elute™ system from Elution Solution (PO Box 5147, Charlottesville, Va. 22905) charged with a 90 g silica gel cartridge (40M FSO-0110-040155, 32-63 μm) at 20 psi ($N_2$). GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: $H_2$ at 40 ml/min., Air at 400 ml/min. Carrier gas: Split Ratio 16:1, $N_2$ flow at 15 ml/min., $N_2$ velocity at 18 cm/sec. The temperature program is 70° C. for 0-3 min, 70-300° C. from 3-10 min, 300° C. from 10-15 min.

HPLC analysis was performed on a Gilson 322 Pump, detector UV/Vis-156 at 360 nm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

Synthesis of N-(3,5-diamino-6-chloropyrazine-2-carbonyl)-N'-(4-{4-[3-(1H-tetrazol-5-yl)propoxy]phenyl}butyl)guanidine hydrochloride (PSA 17926)

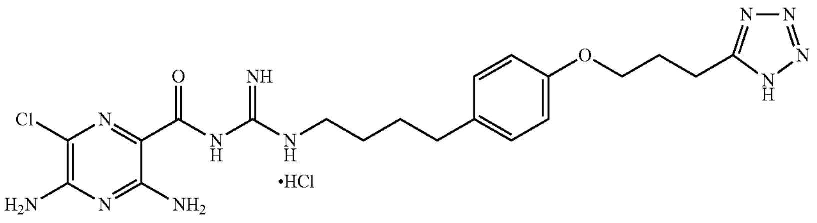

PSA 17926

{4-[4-(3-Cyanopropoxy)phenyl]butyl}carbamic acid benzyl ester (2)

A mixture of [4-(4-hydroxyphenyl)butyl]carbamic acid benzyl ester 1 (2.00 g, 6.70 mmol), 4-bromobutyronitrile (0.70 mL, 6.70 mmol), and potassium carbonate (1.00 g, 7.4 mmol) in DMF (10 mL), was stirred at 65° C. for 16 h. Solvent was removed by rotary evaporation and the residue was taken up in ethyl acetate, washed with water and brine, and concentrated under vacuum. The crude product was purified by flash silica gel column chromatography eluting with ethyl acetate/$CH_2Cl_2$ (1:9, v/v) to give the desired product 2 as a white solid (1.80 g, 75% yield). $^1$H NMR (300 MHz, $CDCl_3$) δ 1.56 (m, 4H), 2.15 (m, 2H), 2.55 (m, 4H), 3.15 (m, 2H), 4.00 (m, 2H), 4.70 (br s, 1H), 5.10 (s, 2H), 6.80 (d, 2H), 7.05 (d, 2H), 7.30 (m, 5H). m/z (ESI): 367 $[C_{22}H_{26}N_2O_3+H]^+$.

(4-{-4-[3-(1H-Tetrazol-5-yl)propoxy]phenyl}butyl)carbamic acid benzyl ester (3)

A mixture of {4-[4-(3-cyanopropoxy)phenyl]butyl}carbamic acid benzyl ester 2 (0.90 g, 2.5 mmol), sodium azide (0.50 g, 7.5 mmol), and ammonium chloride (0.40 g, 7.5 mmol) in DMF (7 mL), was stirred at 120° C. for 16 h. Inorganics were removed by vacuum filtration. The filtrate was diluted with ethyl acetate, and washed with water and brine. The organic solution was dried over $Na_2SO_4$, filtered and concentrated. The residue was taken up in ethyl acetate (5 mL) and diluted with hexanes (10 mL). Solid precipitates were collected by suction filtration and purified by flash silica gel column chromatography eluting with methanol/dichloromethane (1:50, v/v) to give the desired product 3 as a white solid (0.78 g, 76% yield). $^1$H NMR (300 MHz, $CD_3OD$) δ 1.51 (m, 4H), 2.20 (m, 2H), 2.50 (m, 2H), 3.10 (m, 4H), 4.00 (m, 2H), 5.00 (s, 2H), 6.75 (d, 2H), 7.05 (d, 2H), 7.30 (m, 5H). m/z (ESI): 410 $[C_{22}H_{27}N_5O_3+H]^+$.

4-{4-[3-(1H-Tetrazol-5-yl)propoxy]phenyl}butylamine (4)

A solution of (4-{4-[3-(1H-tetrazol-5-yl)propoxy]phenyl}butyl)carbamic acid benzyl ester 3 (0.30 g, 0.73 mmol) in methanol (20 mL) and dichloromethane (5 mL) was stirred at room temperature overnight under hydrogen atmosphere in the presence of 10% palladium-on-carbon catalyst (0.1 g, 50% wet). The catalyst was removed by suction filtration, and the filtrate was concentrated in vacuo to give the desired product 4 as a white solid (200 mg, 99% yield) which was used for the next step without further purification. m/z (ESI): 276 $[C_{14}H_{21}N_5O+H]^+$.

N-(3,5-Diamino-6-chloropyrazine-2-carbonyl)-N'-(4-{4-[3-(1H-tetrazol-5-yl)-propoxy]phenyl}butyl)guanidine hydrochloride (5, PSA 17926)

A solution of 4-{4-[3-(1H-tetrazol-5-yl)propoxy]phenyl}butylamine 4 (100 mg, 0.36 mmol) and triethylamine (0.15 mL, 0.39 mmol) in absolute ethanol (2 mL) was stirred at 60° C. for 5 min, after which 1-(3,5-diamino-6-chloropyrazine-2-carbonyl)-2-methyl-isothiourea hydriodide (150 mg, 0.39 mmol) was added in one portion. The reaction mixture was stirred at that temperature for 4 h and then cooled to room temperature. The reaction mixture was concentrated by rotary evaporation. The crude residue was washed with water and filtered. The filter cake was further washed with dichloromethane. A dark yellow solid (140 mg, 80% yield) thus obtained was slurried in a mixture of methanol and dichloromethane (5/95, v/v). The solid was collected by suction filtration, and 40 mg of such solid was mixed with 3% aqueous HCl (4 mL). The mixture was sonicated, stirred at room temperature for 15 min and filtered. The filter cake was dried under high vacuum to give N-(3,5-diamino-6-chloropyrazine-2-carbonyl)-N'-(4-{4-[3-(1H-tetrazol-5-yl)propoxy]phenyl}butyl)guanidine hydrochloride (5, PSA 17926) as a yellow solid. mp 125-127° C. (decomposed). $^1$H NMR (300 MHz, $CD_3OD$) δ 1.70 (m, 4H), 2.22 (m, 2H), 2.60 (m, 2H), 3.10 (m, 2H), 4.00 (m, 2H), 6.70 (d, 2H), 7.09 (d, 2H). m/z (ESI): 488 $[C_{20}H_{26}ClN_{11}O_2+H]^+$.

Example 2

Synthesis of dimethylthiocarbamic acid O-(4-{4-[N'-(3,5-diamino-6-chloropyrazine-2-carbonyl)guanidino]butyl}phenyl) ester (PSA 17846)

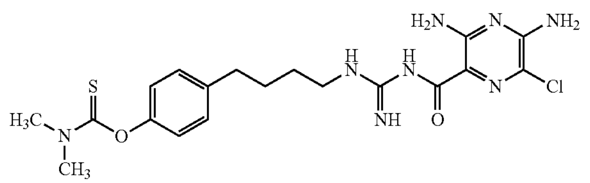

PSA 17846

2-[4-(4-Hydroxyphenyl)butyl]isoindole-1,3-dione (8)

A mixture of 4-(4-aminobutyl)phenol hydrobromide 6 (8.2 g, 33.5 mmol), phthalic anhydride 7 (5.0 g, 33.8 mmol), and triethylamine (4.6 mL, 33.5 mmol) in chloroform (50 mL) was stirred at reflux for 18 h, cooled to room temperature and concentrated by rotary evaporation. The residue was dissolved in acetic acid (50 mL) and stirred at 100° C. for 3 h. Solvent was evaporated and the resulting residue was purified by flash silica gel column chromatography eluting with $CH_2Cl_2$/EtOAc/hexanes (8:1:1, v/v) to give the desired product 8 as a white powder (4.1 g, 41% yield). $^1$H NMR (300 MHz, DMSO-$d_6$) δ 1.57 (m, 4H), 2.46 (m, 2H), 3.58 (m, 2H), 6.64 (d, 2H), 6.95 (d, 2H), 7.82 (m, 4H), 9.12 (s, 1H). m/z (ESI): 296 $[C_{18}H_{17}NO_3+H]^+$.

Dimethylthiocarbamic acid O-{4-[4-(1,3-dioxo-1,3-dihydroisoindol-2-yl)butyl]-phenyl}ester (9)

A suspension of sodium hydride (60% in mineral oil, 0.44 g, 0.11 mmol) in anhydrous DMF (10 mL) was cooled to 0° C. and added to a solution of 2-[4-(4-hydroxyphenyl)-butyl]isoindole-1,3-dione 8 (2.95 g, 10 mmol) in DMF (15 mL). The mixture was stirred at 0° C. for 30 min and then at room temperature for an additional one hour. A solution of dimethylthiocarbamic acid chloride (1.35 g, 11 mmol) in DMF (10 mL) was then added. The reaction mixture was stirred at room temperature first for 16 h and then at 50° C. for 1 h, cooled back to room temperature and quenched with methanol (10 mL). The mixture was concentrated under vacuum and the residue was purified by flash silica gel column chromatography eluting with $CH_2Cl_2$/hexanes/EtOAc (10:1:0.2, v/v) to give the desired product 9 as a yellowish solid (2.27 g, 59% yield). $^1$H NMR (300 MHz, $CDCl_3$) δ 1.72 (m, 4H), 2.67 (m, 2H), 3.33 (s, 3H), 3.45 (s, 3H), 3.71 (m, 2H), 6.95 (d, 2H), 7.18 (d, 2H), 7.70 (m, 2H), 7.84 (m, 2H). m/z (ESI): 383 $[C_{21}H_{22}N_2O_3S+H]^+$.

Dimethylthiocarbamic acid O-[4-(4-aminobutyl)phenyl]ester (10)

A mixture of dimethylthiocarbamic acid O-{4-[4-(1,3-dioxo-1,3-dihydroisoindol-2-yl)-butyl]phenyl}ester 9 (0.30 g, 0.80 mmol) and methylamine (2M in methanol, 10 mL, 20 mmol) was stirred at room temperature overnight. Solvent was removed by rotary evaporation and the residue was purified by flash silica gel column chromatography (Biotage) eluting with chloroform/methanol/concentrated ammonium hydroxide (10:1:0.1, v/v) to give dimethylthiocarbamic acid O-[4-(4-aminobutyl)phenyl]ester (10) as a clear colorless oil (118 mg, 46% yield). $^1$H NMR (300 MHz, $CD_3OD$) δ 1.70 (m, 4H), 2.70 (m, 4H), 3.34 (s, 3H), 3.46 (s, 3H), 6.96 (d, 2H), 7.20 (d, 2H). m/z (ESI): 253 $[C_{13}H_{20}N_2OS+H]^+$.

Dimethylthiocarbamic acid O-(4-{4-[N'-(3,5-diamino-6-chloropyrazine-2-carbonyl)-guanidino]butyl}phenyl) ester (11, PSA 17846)

A solution of dimethylthiocarbamic acid O-[4-(4-aminobutyl)phenyl]ester 10 (115 mg, 0.45 mmol), triethylamine (0.30 mL, 2.2 mmol), and 1-(3,5-diamino-6-chloropyrazine-2-carbonyl)-2-methylisothiourea hydriodide (175 mg, 0.45 mmol) in anhydrous THF (6 mL) was stirred at reflux for 3 h and then cooled to room temperature. The reaction mixture was concentrated by rotary evaporation. The crude residue was purified by flash silica gel column chromatography (Biotage) eluting with chloroform/methanol/concentrated ammonium hydroxide (15:1:0.1, v/v) to give the desired product 11 as a yellow solid (180 mg, 86% yield). mp 102-105° C. $^1$H NMR (300 MHz, $CD_3OD$) δ 1.70 (m, 4H), 2.65

(m, 2H), 3.20 (m, 2H), 3.30 (s, 3H), 3.40 (s, 3H), 6.95 (d, 2H), 7.20 (d, 2H). m/z (ESI): 465 $[C_{19}H_{25}ClN_8O_2S+H]^+$.

Example 3

Synthesis of (2S)-(4-{-4-[N'-(3,5-diamino-6-chloropyrazine-2-carbonyl)guanidino]-butyl}benzenesulfonylamino)-3-methylbutyramide (PSA 19008)

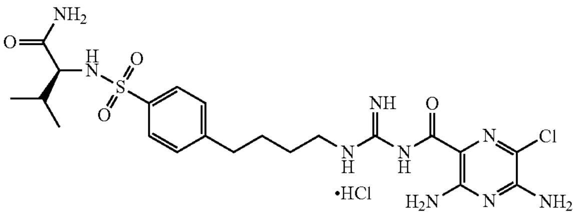

PSA 19008

4-[4-(1,3-Dioxo-1,3-dihydroisoindol-2-yl)butyl]benzenesulfonyl chloride (13)

2-(4-Phenylbutyl)isoindole-1,3-dione 12 (1.9 g, 6.8 mmol) was added to chlorosulfonic acid (10 mL, 138 mmol) at 0° C. and the mixture was stirred for 1 h at the temperature. After storing in refrigerator at −5° C. overnight, the reaction mixture was poured onto crushed ice (100 g) and precipitates were collected by a suction filtration and dried under high vacuum to afford the desired product 13 (2.48 g, 99% yield). $^1$H NMR (300 MHz, $CDCl_3$) δ 1.70 (m, 4H), 2.78 (m, 2H), 3.70 (m, 2H), 7.40 (d, 2H) 7.70 (d, 2H), 7.85 (d, 2H), 7.95 (d, 2H).

(2S)-{4-[4-(1,3-Dioxo-1,3-dihydroisoindol-2-yl)butyl]benzenesulfonylamino}-3-methylbutyramide (14)

4-[4-(1,3-Dioxo-1,3-dihydroisoindol-2-yl)butyl]benzenesulfonyl chloride 13 (0.45 g, 1.19 mmol) was dissolved in dry DMF (5 mL), and added to a solution of N-methylmorpholine (3 mL) and (2S)-amino-3-methylbutyramide (0.18 g, 1.19 mmol) in DMF (10 mL). The reaction mixture was stirred at room temperature for 66 h. Solvent was removed by rotary evaporation and the residue was purified by flash silica gel chromatography eluting with chloroform/methanol/concentrated ammonium hydroxide (15:1:0.1, v/v) to give the desired product 14 as a white powder (0.41 g, 73% yield). $^1$H NMR (300 MHz, DMSO-$d_6$) δ 0.72 (d, 3H), 0.76 (d, 3H), 1.77 (m, 4H), 1.79 (m, 1H), 2.68 (m, 2H), 3.40 (m, 1H), 3.60 (m, 2H), 6.92 (s, 1H), 7.21 (s, 1H), 7.34 (d, 2H) 7.50 (d, 1H), 7.65 (d, 2H), 7.82 (m, 4H).

(2S)-[4-(4-Aminobutyl)benzenesulfonyl amino]-3-methylbutyramide (15)

A mixture of (2S)-{4-[4-(1,3-dioxo-1,3-dihydroisoindol-2-yl)butyl]-benzenesulfonylamino}-3-methylbutyramide 14 (0.40 g, 0.87 mmol) and methylamine (2 M in methanol, 20 mL, 40 mmol) was stirred at room temperature overnight. Solvent was removed by rotary evaporation and the residue was purified by flash silica gel column chromatography eluting with chloroform/methanol/concentrated ammonium hydroxide (3:1:0.1, v/v) to give (2S)-[4-(4-aminobutyl)benzenesulfonylamino]-3-methyl-butyramide (15) as a white powder (156 mg, 54% yield). $^1$H NMR (300 MHz, $CD_3OD$) δ 0.85 (d, 3H), 0.87 (d, 3H), 1.66 (m, 4H), 1.90 (m, 1H), 2.69 (m, 4H), 3.51 (d, 1H), 7.35 (d, 2H) 7.75 (d, 2H). m/z (ESI): 328 $[C_{15}H_{25}N_3O_3S+H]^+$.

(2S)-(4-{4-[N'-(3,5-Diamino-6-chloropyrazine-2-carbonyl)guanidino]butyl}-benzenesulfonylamino)-3-methylbutyramide (16, PSA 19008)

A solution of (2S)-[4-(4-aminobutyl)benzenesulfonylamino]-3-methylbutyramide 15 (156 mg, 0.47 mmol), diisopropylethylamine (0.60 mL, 3.0 mmol), and 1-(3,5-diamino-6-chloropyrazine-2-carbonyl)-2-methylisothiourea hydriodide (230 mg, 0.61 mmol) in absolute ethanol (8 mL) was stirred at 70° C. for 5 h and then cooled to room temperature. The reaction mixture was concentrated by rotary evaporation. The crude residue was washed with water, filtered and the crude solid product was purified by flash silica gel column chromatography eluting with chloroform/methanol/concentrated ammonium hydroxide (5:1:0.1, v/v) to give the desired product as a yellow solid (137 mg, 54% yield). Part of the solid (86 mg) was further purified by semi-preparative HPLC (acetonitrile/water/0.1% TFA) to give the analytical pure sample which was then co-evaporated with 5% aqueous HCl to give the hydrochloride salt 16. mp 154-156° C. (decomposed). $^1$H NMR (300 MHz, $CD_3OD$) δ 0.85 (d, 3H), 0.86 (d, 3H), 1.70 (m, 4H), 1.90 (m, 1H), 2.75 (m, 2H), 3.32 (m, 2H), 3.52 (d, 1H), 7.35 (d, 2H), 7.75 (d, 2H). m/z (ESI): 540 $[C_{21}H_{30}ClN_9O_4S+H]^+$. $[\alpha]_D^{25}$+5.2° (c 0.50, MeOH).

Example 4

Synthesis of 2-(4-{4-[N'-(3,5-diamino-6-chloropyrazine-2-carbonyl)guanidino]-butyl}phenoxy)-N-phenylacetamide (PSA 17482)

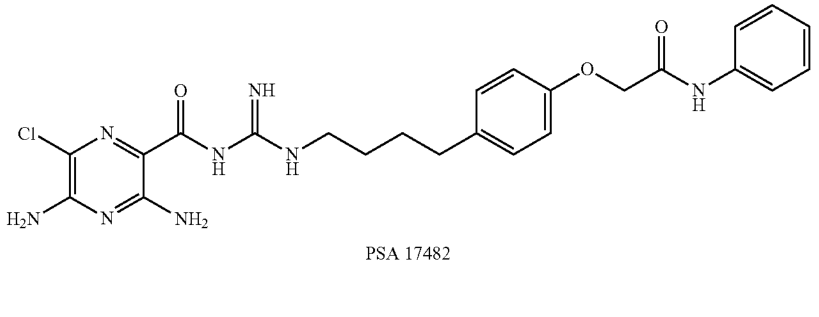 [SMILES: N=C(NCCCCc1ccc(OCC(=O)Nc2ccccc2)cc1)NC(=O)c1nc(Cl)c(N)nc1N]

PSA 17482

[4-(4-Phenylcarbamoylmethoxyphenyl)butyl]carbamic acid benzyl ester (18)

A mixture of [4-(4-benzyloxycarbonylaminobutyl)phenoxy]acetic acid (300 mg, 0.84 mmol), aniline (0.15 mL, 1.70 mmol), DMAP (60 mg, 0.50 mmol) and EDC.HCl (320 mg, 1.70 mmol) in $CH_2Cl_2$ (30 mL) was stirred at room temperature for 66 h. The reaction mixture was concentrated under vacuum and the residue was subjected to flash silica gel column chromatography eluting with methanol/$CH_2Cl_2$ (1:99, v/v) to give the desired amide 18 as a white solid (360 mg, 99% yield). $^1$H NMR (300 MHz, $CDCl_3$) δ 1.55 (m, 4H), 2.60 (m, 2H), 3.20 (m, 2H), 4.58 (s, 2H), 4.70 (br s, 1H), 5.10 (s, 2H), 6.88 (d, 2H), 7.15 (m, 3H), 7.35 (m, 7H), 7.58 (d, 2H), 8.25 (s, 1H). m/z (ESI): 433 $[C_{26}H_{28}N_2O_4+H]^+$.

2-[4-(4-Aminobutyl)phenoxy]-N-phenylacetamide (19)

A solution of [4-(4-phenylcarbamoylmethoxyphenyl)butyl]carbamic acid benzyl ester 18 (0.30 g, 0.69 mmol) in ethanol (10 mL), THF (6 mL), and acetic acid (2 mL) was stirred at room temperature for 2 h under hydrogen atmosphere in the presence of 10% Pd/C catalyst (0.2 g, 50% wet). The catalyst was removed by suction filtration and the filtrate was concentrated in vacuo. The residue was purified by flash silica gel column chromatography eluting with $CH_2Cl_2$/methanol/concentrated ammonium hydroxide (30:1:0, 30:1:0.3, v/v) to give the desired amine 19 as a white solid (200 mg, 97% yield). $^1$H NMR (300 MHz, $CD_3OD$) δ 1.60 (m, 4H), 2.55 (m, 2H), 2.70 (m, 2H), 4.60 (s, 2H), 6.88 (d, 2H), 7.15 (m, 3H), 7.35 (m, 2H), 7.58 (d, 2H), 8.25 (s, 1H). m/z (ESI): 299 $[C_{18}H_{22}N_2O_2+H]^+$.

2-(4-{4[N'-(3,5-Diamino-6-chloropyrazine-2-carbonyl)guanidino]butyl}phenoxy)-N-phenylacetamide (20, PSA 17482)

A solution of 2-[4-(4-aminobutyl)phenoxy]-N-phenylacetamide 19 (100 mg, 0.35 mmol) and triethylamine (0.14 mL, 1.00 mmol) in absolute ethanol (2 mL) was stirred at 60° C. for 30 min, after which 1-(3,5-diamino-6-chloropyrazine-2-carbonyl)-2-methyl-isothiourea hydriodide (140 mg, 0.37 mmol) was added in one portion. The reaction mixture was stirred at that temperature for 4 h, cooled to room temperature, and concentrated by rotary evaporation. The crude residue was triturated with water and filtered. The filter cake was purified by flash silica gel column chromatography eluting with dichloromethane/methanol/concentrated ammonium hydroxide (500:10:0, 500:10:1, 200:10:1, v/v) to give 2-(4-{4-[N'-(3,5-diamino-6-chloro-pyrazine-2-carbonyl)guanidino]butyl}phenoxy)-N-phenylacetamide (20, PSA 17482) as a yellow solid (120 mg, 67% yield). mp 168-170° C. $^1$H NMR (300 MHz, DMSO-$d_6$) δ 1.55 (m, 4H), 2.55 (m, 2H), 3.16 (m, 2H), 4.65 (s, 2H), 6.60 (br s, 2H), 6.90 (d, 2H), 7.08 (m, 2H), 7.15 (d, 2H), 7.30 (m, 5H), 7.60 (d, 2H), 9.00 (br s, 1H), 10.00 (br s, 1H). m/z (ESI): 511 $[C_{24}H_{27}ClN_8O_3+H]^+$.

Example 5

Synthesis of N-(3,5-diamino-6-chloropyrazine-2-carbonyl)-N'-(4-{4-[3-(1H-imidazol-2-yl)propoxy]phenyl}butyl)guanidine (PSA 23022)

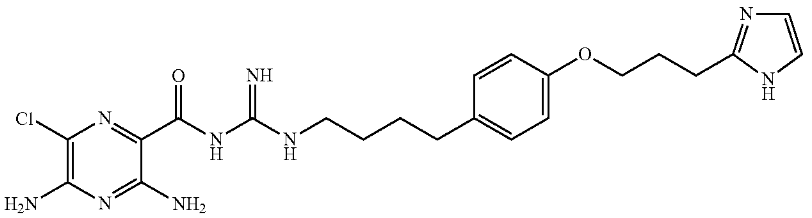

PSA 23022

4-{4-[3-(1H-Imidazol-2-yl)propoxy]phenyl}butylamine (21)

Compound 2 (0.156 g, 0.425 mmol) was dissolved in anhydrous ethanol (10 mL). To the solution was bubbled anhydrous HCl gas for 3 min. The reaction vessel was sealed and the mixture was stirred at room temperature for 48 h, and then concentrated to dryness under vacuum. The resulting residue was dissolved in anhydrous methanol (5 mL). To the newly formed solution was added 2,2-dimethoxyethylamine (0.097 mL, 0.891 mmol) in one portion. After stirring at room temperature overnight, temperature was raised to reflux which was maintained for another 3 h before the mixture was cooled to ambient temperature. Solvent was removed under vacuum and the residue was treated with 1.2 N HCl aqueous solution at 80° C. for 2 hours. The mixture was then cooled to ambient temperature again and neutralized to pH ~9 with powder $K_2CO_3$. Water was completely removed under vacuum and the residue was dissolved in methanol. The methanol solution was loaded onto silica gel, and the product was eluted with a mixture of concentrated ammonium hydroxide/MeOH/$CH_2Cl_2$ (1.8:18:81.2, v/v), affording the product 21 (27 mg, 23% overall yield) as an off-white solid. $^1$H NMR (300 MHz, $CD_3OD$): δ 1.60 (m, 4H), 2.14 (m, 2H), 2.56 (t, 2H), 2.76 (t, 2H), 2.86 (t, 2H), 3.94 (t, 2H), 6.79 (d, 2H), 6.91 (s, 2H), 7.08 (d, 2H). m/z (APCI): 274 $[C_{16}H_{23}N_3O+H]^+$.

N-(3,5-Diamino-6-chloropyrazine-2-carbonyl)-N'-(4-{4-[3-(1H-imidazol-2-yl)propoxy]phenyl}butyl)guanidine (22, PSA 23022)

Compound 21 (23 mg, 0.084 mmol) was dissolved in a mixture of ethanol (3 mL) and Hunig's base (0.074 mL, 0.421 mmol) at 65° C. over 15 min. To the solution was added 1-(3,5-diamino-6-chloropyrazine-2-carbonyl)-2-methyl-isothiourea hydriodide (43 mg, 0.109 mmol) and the resulting mixture was stirred at the above temperature for an additional 3 h before all liquid was removed under vacuum. The residue was chromatographed on silica gel, eluting with a mixture of concentrated ammonium hydroxide/methanol/dichloromethane (1.5:15:63.5, v/v), to afford the desired product 22 (34 mg, 83% yield) as a yellow solid. mp 123-126° C. (decomposed), $^1$H NMR (300 MHz, $CD_3OD$): δ 1.62 (m, 4H), 2.14 (m, 2H), 2.58 (t, 2H), 2.88 (t, 2H), 3.21 (t, 2H), 3.94 (t, 2H), 6.77 (d, 2H), 6.90 (s, 2H), 7.06 (d, 2H). m/z (APCI): 486 $[C_{22}H_{28}ClN_9O_2+H]^+$.

Example 6

Synthesis of 2-(4-{4-[N'-(3,5-diamino-6-chloropyrazine-2-carbonyl)guanidino]-butyl}phenoxy)-N,N-bis-(2-hydroxyethyl)acetamide (PSA 16826)

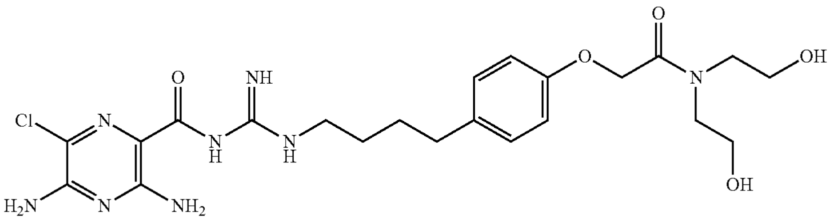

PSA 16826

[4-(4-{[N,N-Bis-(2-hydroxyethyl)carbamoyl]methoxy}phenyl)butyl]carbamic acid benzyl ester (25)

A solution of [4-(4-benzyloxycarbonylaminobutyl)phenoxy]acetic acid ethyl ester 23 (0.3 g, 0.78 mmol), 2-(2-hydroxyethylamino)ethanol 24 (0.15 mL, 1.6 mmol), and ethanol (20 mL) was heated at 70° C. for 72 hours. Solvent was evaporated in vacuo. The residue was purified by flash chromatography (silica gel, dichloromethane/methanol, 100:5, v/v) to provide [4-(4-{[N,N-bis-(2-hydroxyethyl)carbamoyl]methoxy}phenyl)-butyl]carbamic acid benzyl ester 25 [0.19 g, 100% based on the recovered starting material (0.13 g)] as a pale yellow solid. $^1$H NMR (300 MHz, $CD_3OD$) δ 1.65 (m, 4H), 2.50 (m, 2H), 3.20 (m, 2H), 3.55 (m, 4H), 3.75 (m, 4H), 4.80 (s, 2H), 5.10 (s, 2H), 6.85 (d, 2H), 7.10 (d, 2H), 7.40 (m, 5H). m/z (ESI): 445 $[C_{24}H_{32}N_2)_6+H]^+$.

2-[4-(4-Aminobutyl)phenoxy]-N,N-bis-(2-hydroxyethyl)acetamide (26)

To a degassed solution of [4-(4-{[N,N-bis-(2-hydroxyethyl)carbamoyl]methoxy}phenyl)-butyl]carbamic acid benzyl ester 25 (0.19 g, 0.43 mmol) in ethanol (4 mL) was added 10% palladium on activated carbon (0.1 g, 50% wet). The mixture was hydrogenated overnight at atmospheric hydrogen. The catalyst was filtered through a pad of diatomaceous earth and the solvent was evaporated in vacuo. The residue was purified by flash chromatography (silica gel, 20-5:1:0.1-1 dichloromethane/methanol/concentrated ammonium hydroxide, v/v) to provide 26 (0.09 g, 72%) as a colorless oil. $^1$H NMR (300 MHz, $CD_3OD$) δ 1.56 (m, 4H), 2.56 (t, 2H), 2.65 (t, 1H), 3.29 (m, 1H), 3.55 (m, 4H), 3.72 (m, 4H), 4.90 (s, 2H), 6.86 (d, 2H), 7.09 (d, 2H). m/z (ESI): 311 $[C_{16}H_{26}N_2O_4+H]^+$.

2-(4-{4-[N'-(3,5-Diamino-6-chloropyrazine-2-carbonyl)guanidino]butyl}phenoxy)-N,N-bis-(2-hydroxyethyl)acetamide (27, PSA 16826)

1-(3,5-Diamino-6-chloropyrazine-2-carbonyl)-2-methylisothiourea hydriodide (0.13 g, 0.33 mmol) was added to a solution of 2-[4-(4-aminobutyl)phenoxy]-N,N-bis-(2-hydroxyethyl)acetamide 26 (0.09 g, 0.3 mmol), triethylamine (0.12 mL), and ethanol (1.7 mL). The reaction mixture was stirred at 60° C. for 3 h. The solvent was evaporated in vacuo. The residue was triturated with water and then purified by flash chromatography (silica gel, 20-10:1:0-0.2 $CH_2Cl_2$/methanol/concentrated ammonium hydroxide, v/v) to provide 2-(4-{4-[N'-(3,5-diamino-6-chloropyrazine-2-carbonyl)guanidino]butyl}-phenoxy)-N,N-bis-(2-hydroxyethyl)acetamide 27 (0.1 g, 64%) as a yellow solid. mp 114-1.16° C. $^1$H NMR (300 MHz, $CD_3OD$) δ 1.70 (m, 4H), 2.60 (m, 2H), 3.32 (m, 2H), 3.50 (m, 4H), 3.70 (m, 4H), 4.81 (s, 2H), 6.85 (d, 2H), 7.10 (d, 2H). m/z (ESI): 523 $[C_{22}H_{31}ClN_8O_5+H]^+$.

Example 7

Synthesis of 2-(4-{4-[N'-(3,5-diamino-6-chloropyrazine-2-carbonyl)guanidino]-butyl}phenoxy)-N,N-dimethylacetamide hydrochloride (PSA 16313)

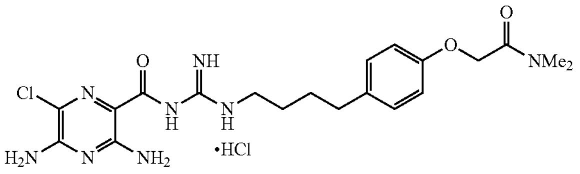

PSA 16313

[4-(4-Dimethylcarbamoylmethoxyphenyl)butyl]carbamic acid benzyl ester (28)

A mixture of [4-(4-benzyloxycarbonylaminobutyl)phenoxy]acetic acid ethyl ester 23 (0.50 g, 1.3 mmol) and dimethylamine (2.0 M in THF, 10 mL, 20 mmol) in a sealed tube was heated at 55° C. for 48 h. The solvent was evaporated in vacuo. The residue was purified by flash chromatography (silica gel, ethyl acetate/$CH_2Cl_2$, 1:4, 1:3, v/v) to provide [4-(4-dimethylcarbamoylmethoxyphenyl)butyl]carbamic acid benzyl ester 28 (0.26 g, 52% yield) as a white solid. $^1$H NMR (300 MHz, $CDCl_3$) δ 1.55 (m, 4H), 2.55 (m, 2H), 2.90 (s, 3H), 3.05 (s, 3H), 3.20 (m, 2H), 4.65 (s, 2H), 5.08 (s, 2H), 6.80 (d, 2H), 7.05 (d, 2H), 7.35 (m, 5H).

2-[4-(4-Aminobutyl)phenoxy]-N,N-dimethylacetamide (29)

To a degassed solution of [4-(4-dimethylcarbamoylmethoxyphenyl)butyl]carbamic acid benzyl ester (28) (0.26 g, 0.68 mmol) in ethanol (10 mL) was added 10% palladium on activated carbon (0.1 g, 50% wet). The mixture was stirred at room temperature overnight under atmospheric hydrogen.

The catalyst was filtered through a pad of diatomaceous earth and the solvent was evaporated in vacuo. The residue was purified by flash chromatography (silica gel, dichloromethane/methanol/concentrated ammonium hydroxide, 100:5:1, v/v) to provide 2-[4-(4-aminobutyl)phenoxy]-N,N-dimethylacetamide 29 (100 mg, 60% yield) as a white solid. $^1$H NMR (300 MHz, $CD_3OD$) δ 1.55 (m, 4H), 2.55 (m, 2H), 2.66 (m, 2H), 2.90 (s, 3H), 3.05 (s, 3H), 4.70 (s, 2H), 6.80 (d, 2H), 7.05 (d, 2H). m/z (ESI): 251 $[C_{14}H_{22}N_2O_2+H]^+$.

2-(4-{4-[N'-(3,5-Diamino-6-chloropyrazine-2-carbonyl)guanidino]butyl}phenoxy)-N,N-dimethylacetamide hydrochloride (30, PSA 16313)

A solution of 2-[4-(4-aminobutyl)phenoxy]-N,N-dimethylacetamide 29 (67 mg, 0.27 mmol) in absolute ethanol (1 mL) was stirred at 65° C. for 30 min, after which 1-(3,5-diamino-6-chloropyrazine-2-carbonyl)-2-methylisothiourea hydriodide (110 mg, 0.29 mmol) was added in one portion. The reaction mixture was stirred at that temperature for 3 h and then cooled to room temperature. The reaction mixture was concentrated by rotary evaporation. The crude residue was triturated with water and filtered. The filter cake was purified by flash silica gel column chromatography eluting with dichloromethane/methanol/concentrated ammonium hydroxide (200:10:0, 200:10:1, v/v) to give 2-(4-{-4-[N'-(3,5-diamino-6-chloropyrazine-2-carbonyl)guanidino]butyl}-phenoxy)-N,N-dimethylacetamide as a yellow solid (35 mg, 28% yield). This solid was dissolved in methanol (2 mL) and added to 4 N aqueous HCl (4 drops). Concentration in vacuo gave 2-(4-{4-[N'-(3,5-diamino-6-chloropyrazine-2-carbonyl)-guanidino]butyl}phenoxy)-N,N-dimethylacetamide hydrochloride (30, PSA 16313). mp 130-132° C. (decomposed). $^1$H NMR (300 MHz, $CD_3OD$) δ 1.69 (m, 4H), 2.60 (m, 2H), 2.95 (s, 3H), 3.10 (s, 3H), 3.35 (m, 2H), 4.75 (s, 2H), 6.80 (d, 2H), 7.10 (d, 2H). m/z (EST): 463 $[C_{20}H_{27}ClN_8O_3+H]^+$.

Example 8

Synthesis of 2-(4-{-4-[N'-(3,5-diamino-6-chloropyrazine-2-carbonyl)guanidino]-butyl}phenoxy)-N-(1H-imidazol-2-yl)acetamide dihydrochloride (PSA 16437)

and hexanes (20 mL), washed with water (20 mL×4) and brine (30 mL), and concentrated under reduced pressure to afford the desired product 32 as a yellow oil (1.28 g, 100% yield) which was used for the next step without further purification. $^1$H NMR (300 MHz, $CDCl_3$) δ 1.40 (s, 9H), 1.41-1.65 (m, 4H), 2.49-2.60 (m, 2H), 3.02-3.16 (m, 2H), 3.79 (s, 3H), 4.45 (br s, 1H), 4.59 (s, 2H), 6.79 (d, 2H), 7.05 (d, 2H). m/z (ESI): 338 $[C_{18}H_{27}NO_5+H]^+$.

[4-(4-tert-Butoxycarbonylaminobutyl)phenoxy]acetic acid (33)

A solution of [4-(4-tert-butoxycarbonylaminobutyl)phenoxy]acetic acid methyl ester 32 (1.28 g, 3.78 mmol) in methanol (80 mL) was added with crushed potassium hydroxide (2.50 g, 85%, 37.8 mmol) and the mixture was stirred at room temperature for 5 h. Solvent was removed by rotary evaporation. The residue was taken up in water and acidified to pH ~1 with 6N aqueous HCl, and extracted with dichloromethane. The combined organics were washed with brine, dried over $Na_2SO_4$, and concentrated to complete dryness to afford the desired product 33 as a white solid (1.19 g, 97% yield). $^1$H NMR (300 MHz, $CD_3OD$) δ 1.41 (s, 9H), 1.42-1.70 (m, 4H), 2.45-2.60 (m, 2H), 3.00-3.20 (m, 2H), 4.60 (s, 2H), 6.80 (d, 2H), 7.08 (d, 2H). m/z (ESI): 322 $[C_{17}H_{25}NO_5-H]^-$.

(4-{4-[(1H-Imidazol-2-yl-carbamoyl)methoxy]phenyl}butyl)carbamic acid tert-butyl ester (34)

[4-(4-tert-Butoxycarbonylaminobutyl)phenoxy]acetic acid 33 (1.19 g, 3.68 mmol) was dissolved in anhydrous THF (10 mL), $CH_2Cl_2$ (10 mL) and $CH_3CN$ (5 mL). To the solution were sequentially added HOAt (200 mg, 1.47 mmol), DMAP (135 mg, 1.10 mmol), and diisopropylethylamine (3.2 mL, 18.40 mmol), followed by the addition of EDC.HCl (1.03 g, 5.35 mmol). The reaction mixture was stirred at room temperature for 15 min. Amino imidazole sulfate (583 mg, 4.41 mmol) was then added and stirring was continued for 48 h. Solvents were removed by rotary evaporation. The residue was taken up in $CH_2Cl_2$ (250 mL), washed with water and brine, and concentrated under reduced pressure. Flash silica gel column chromatography eluting with methanol/dichloromethane (1:30, 1:20, v/v) gave the desired amide as a white solid (0.95 g, 66% yield). $^1$H NMR (300 MHz, $CD_3OD$) δ

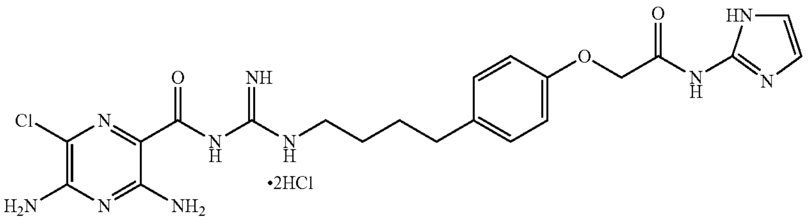

PSA 16437

[4-(4-tert-Butoxycarbonylaminobutyl)phenoxy]acetic acid methyl ester (32)

A mixture of [4-(4-hydroxyphenyl)butyl]carbamic acid tert-butyl ester 31 (1.00 g, 3.78 mmol), potassium carbonate (0.627 g, 4.54 mmol), sodium iodide (0.567 g, 3.78 mmol), and methyl bromoacetate (0.40 mL, 4.21 mmol) in anhydrous DMF (8 mL) was stirred at room temperature for 14 h. The reaction mixture was then diluted with ethyl acetate (100 mL)

1.40 (s, 9H), 1.42-1.70 (m, 4H), 2.48-2.60 (m, 2H), 3.00-3.20 (m, 2H), 4.65 (s, 2H), 6.79-6.89 (m, 4H), 7.10 (d, 2H). m/z (ESI): 389 $[C_{20}H_{28}N_4O_4+H]^-$.

2-[4-(4-Aminobutyl)phenoxy]-N-(1H-imidazol-2-yl)acetamide dihydrochloride (35)

(4-{4-[(1H-Imidazol-2-yl-carbamoyl)methoxy]phenyl}butyl)carbamic acid tert-butyl ester 34 (950 mg, 2.45 mmol) was treated with HCl (4 M in dioxane, 24 mL, 96 mmol) at room temperature for 12 h. The reaction mixture was concentrated in vacuo and further co-evaporated with dichloromethane and methanol, and dried under high vacuum. The desired product was obtained as a white solid (779 mg, 98%) and used directly without further purification. $^1$H NMR (300 MHz, CD$_3$OD) δ 1.59-1.74 (m, 4H), 2.55-2.67 (m, 2H), 2.85-2.98 (m, 2H), 4.80 (s, 2H), 7.00 (d, 2H), 7.18 (d, 2H), 7.19 (s, 2H). m/z (ESI): 289 [C$_{15}$H$_{20}$N$_4$O$_2$+H]$^+$.

2-(4-{4-[N'-(3,5-Diamino-6-chloropyrazine-2-carbonyl)guanidino]butyl}phenoxy)-N-(1H-imidazol-2-yl) acetamide dihydrochloride (36, PSA 16437)

A solution of 2-[4-(4-aminobutyl)phenoxy]-N-(1H-imidazol-2-yl)acetamide dihydrochloride 35 (99 mg, 0.27 mmol) and diisopropylethylamine (0.27 mL, 1.53 mmol) in absolute ethanol (4 mL) and anhydrous methanol (3 mL) was stirred at 70° C. for 30 min, after which 1-(3,5-diamino-6-chloropyrazine-2-carbonyl)-2-methylisothiourea hydriodide (130 mg, 0.34 mmol) was added in one portion. The reaction mixture was stirred for 3 h and then cooled to room temperature. The yellow insolubles were removed by suction filtration and the liquid filtrate was concentrated by rotary evaporation. The crude residue was purified by flash silica gel column chromatography eluting with dichloromethane/methanol/concentrated ammonium hydroxide (200:10:0, 200:10:1, 150:10:1, and 100:10:1, v/v) to give 2-(4-{4-[N'-(3,5-diamino-6-chloropyrazine-2-carbonyl)guanidino]butyl}phenoxy)-N-(1H-imidazol-2-yl)-acetamide as a yellow solid (44 mg, 29% yield). The free base thus obtained was dissolved in methanol and treated with 4 drops of 4 N aqueous HCl. The solution was concentrated under reduced pressure and further dried under vacuum to give the final compound 36. mp 172-174° C. $^1$H NMR (300 MHz, CD$_3$OD) δ 1.61-1.77 (m, 4H), 2.58-2.70 (m, 2H), 3.32-3.40 (m, 2H), 4.80 (s, 2H), 7.00 (d, 2H), 7.18 (d, 2H), 7.20 (s, 2H). m/z (ESI): 501 [C$_{21}$H$_{25}$ClN$_{10}$O$_3$+H]$^+$.

Example 9

Synthesis of N-carbamoylmethyl-2-(4-{4-[N'-(3,5-diamino-6-chloropyrazine-2-carbonyl)guanidino]butyl}phenoxy)acetamide (PSA 16314)

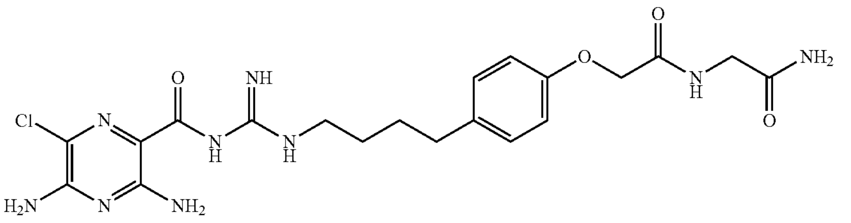

PSA 16314

(4-{4-[(Carbamoylmethylcarbamoyl)methoxy]phenyl}butyl)carbamic acid benzyl ester (37)

Compound 1 (0.50 g, 1.77 mmol) was dissolved in DMF (10 mL). To the solution was added crushed NaOH (0.107 g, 2.66 mmol). The mixture was stirred at room temperature for 30 min. 2-Bromoacetamide (0.367 g, 2.66 mmol) was added. The reaction was further stirred at room temperature overnight, quenched with water (2 mL) and partitioned between water and dichloromethane (each 50 mL). The organic layer was separated, washed with water (2×50 mL), dried over anhydrous Na$_2$SO$_4$ and concentrated under vacuum. The residue was purified on silica gel, eluting with a mixture of methanol/dichloromethane (7:93, v/v), to afford the desired product 37 (0.131 g, 18% yield) as a white solids. $^1$H NMR (300 MHz, CDCl$_3$): δ 1.58 (m, 4H), 2.60 (t, 2H), 3.20 (m, 2H), 4.04 (d, 2H), 4.54 (s, 2H), 4.75 (br, 2H), 5.12 (s, 2H), 5.43 (br, 1H), 5.80 (br, 1H), 6.85 (d, 2H), 7.12 (d, 2H), 7.36 (m, 5H). m/z (APCI): 414 [C$_{22}$H$_{27}$N$_3$O$_5$+H]$^+$.

2-[4-(4-Aminobutyl)phenoxy]-N-carbamoylmethylacetamide (38)

Compound 37 (130 mg, 0.314 mmol) was dissolved in EtOH and THF (14 mL, 1/1 ratio). The reaction vessel was purged with nitrogen both before and after the catalyst (100 mg, 10% Pd/C, 50% wet) was added. The mixture was stirred under hydrogen atmosphere (1 atm) overnight. After purging with nitrogen, the catalyst was vacuum filtered and washed with ethanol (3×5 mL). The combined filtrates were concentrated under vacuum. The residue was chromatographed on silica gel, eluting with a mixture of concentrated ammonium hydroxide/methanol/dichloromethane (2:20:88, v/v), to afford the desired product 38 (80 mg, 91% yield) as a white solid. $^1$H NMR (300 MHz, CD$_3$OD): δ 1.62 (m, 4H), 2.60 (t, 2H), 2.75 (t, 2H), 3.92 (s, 2H), 4.54 (s, 2H), 6.92 (d, 2H), 7.14 (d, 2H).

N-Carbamoylmethyl-2-(4-{4-[N'-(3,5-diamino-6-chloropyrazine-2-carbonyl)-guanidino]butyl}phenoxy)acetamide (39, PSA 16314)

Compound 38 (79 mg, 0.283 mmol) was dissolved in a mixture of absolute ethanol (5 mL) and Hunig's base (0.25 mL, 1.41 mmol) at 65° C. over 10 min. To the solution was added 1-(3,5-diamino-6-chloropyrazine-2-carbonyl)-2-methylisothiourea hydriodide (132 mg, 0.34 mmol) in one portion. The newly resulting reaction mixture was continuously stirred for an additional 2 h before it was cooled down to ambient temperature and subsequently concentrated under vacuum. The resulting residue was purified by chromatography eluting with methanol/dichloromethane/concentrated ammonium hydroxide (10/2/1988, v/v) to afford the free base (93 mg, 67% yield) as a yellow solid. The HCl salt was made using the following procedure: 45 mg of the free base was suspended in ethanol (2 mL) and treated with concentrated HCl (12 N, 0.5 mL) for 10 min. All liquid was then completely removed under vacuum to afford 39 (47 mg). mp 178-180° C. (decomposed). $^1$H NMR (300 MHz, DMSO-d$_6$): δ 1.61 (m, 4H), 2.58 (t, 2H), 3.32 (m, 2H), 3.70 (s, 2H), 4.48 (s, 2H), 6.93 (d, 2H), 7.08 (br, 1H), 7.13 (d, 2H), 7.36 (br, 1H), 7.44 (br, 2H), 8.17 (t, 1H), 8.74 (br, 1H), 8.90 (br, 2H), 9.18 (t, 1H), 10.48 (br, 1H). m/z (APCI): 492 $[C_{20}H_{26}ClN_9O_4+H]^+$.

Example 10

Synthesis of N-[4-(4-cyanomethoxyphenyl)butyl]-N'-(3,5-diamino-6-chloro-pyrazine-2-carbonyl) guanidine (PSA 16208)

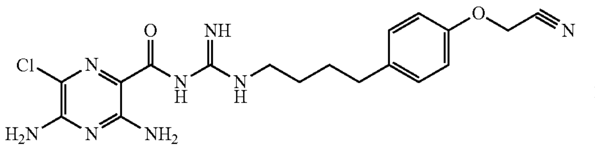

PSA 16208

[4-(4-Cyanomethoxyphenyl)butyl]carbamic acid tert-butyl ester (40)

A mixture of [4-(4-hydroxyphenyl)butyl]carbamic acid tert-butyl ester 31 (0.365 g, 1.37 mmol) and $Cs_2CO_3$ (0.672 g, 2.06 mmol) in anhydrous DMF (8 mL) was heated at 65° C. for 30 min. Iodoacetonitrile (0.276 g, 1.651 mmol) was then added to the mixture in one portion. The mixture was stirred at 65° C. overnight, and then cooled to room temperature. The precipitated solid was filtered, and the filtrate was partitioned between water and dichloromethane (each 50 mL). The organic layer was separated, washed with brine (3×50 mL), dried over anhydrous $Na_2SO_4$ and concentrated under vacuum. The residue was chromatographed on silica gel, eluting with a mixture of diethyl ether/dichloromethane (6:94, v/v), to afford the desired product 40 (0.109 g, 38% yield) as a colorless viscous oil. $^1$H NMR (300 MHz, $CDCl_3$): δ 1.43 (s, 9H), 1.57 (m, 4H), 2.60 (t, 2H), 3.15 (m, 2H), 4.49 (br, 1H), 4.75 (s, 2H), 6.91 (d, 2H), 7.13 (d, 2H).

[4-(4-Aminobutyl)phenoxy]acetonitrile (41)

Compound 40 (0.105 g, 0.345 mmol) was dissolved in dichloromethane (10 mL). Trifluoroacetic acid (2 mL) was added in one portion. The mixture was stirred at room temperature for 2 h, and then concentrated under vacuum to dryness. The crude residue was used directly without further purification. $^1$H NMR (300 MHz, $CD_3OD$): δ 1.60-1.75 (m, 4H), 2.65 (t, 2H), 2.92 (t, 2H), 4.38 (s, 2H), 6.96 (d, 2H), 7.20 (d, 2H). m/z (APCI): 205 $[C_{12}H_{16}N_2O+H]^+$.

N-[4-(4-Cyanomethoxyphenyl)butyl]-N'-(3,5-diamino-6-chloropyrazine-2-carbonyl)guanidine (42, PSA 16208)

A mixture of compound 41 (0.070 g, 0.345 mmol) and Hunig's base (0.3 mL, 1.72 mmol) in anhydrous ethanol was heated at 65° C. for 20 min. To the solution was added 1-(3,5-diamino-6-chloropyrazine-2-carbonyl)-2-methylisothiourea hydriodide (0.148 g, 0.379 mmol) in one portion. The heating was continued for another 2 h. The reaction mixture was then concentrated under vacuum. The residue was chromatographed by flash column chromatography and further purified by preparative TLC, eluting with methanol/dichloromethane/concentrated ammonium hydroxide (10/1/89, v/v), to afford the desired product 42 (0.031 g, 22%) as a yellow solid. mp 129-132° C. $^1$H NMR (300 MHz, $CD_3OD$): δ 1.72 (m, 4H), 2.68 (t, 2H), 3.32 (m, 2H), 4.92 (s, 2H), 6.95 (d, 2H), 7.22 (d, 2H); m/z (APCI): 417 $[C_{18}H_{21}ClN_8O_2+H]^+$.

Example 11

Synthesis of N-(3,5-diamino-6-chloropyrazine-2-carbonyl)-N'-(4-{4-[3-(2,3-dihydroxypropoxy)-2-hydroxypropoxy]phenyl}butyl)guanidine (PSA 15143)

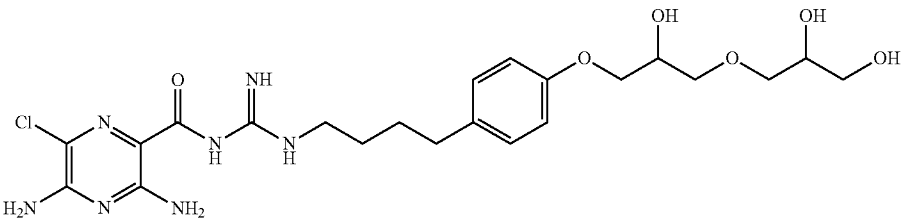

PSA 15143

(4-{4-[3-(2,3-Dihydroxypropoxy)-2-hydroxypropoxy]phenyl}butyl)carbamic acid benzyl ester (43)

A solution containing compound 1 (2.0 g, 6.68 mmol), triethylamine (0.093 mL, 0.668 mmol) and anhydrous ethanol (2.2 mL) was heated at 70° C. for 1 h. Oxiranylmethanol (0.5 mL, 6.68 mmol) was added every hour for a total of 4 h (the total amount of oxiranylmethanol added was 2.0 ml, 26.72 mmol). The reaction was concentrated under vacuum. The residue was chromatographed on silica gel with the elution of a mixture of methanol/dichloromethane (3:97, v/v) to provide 168 mg (4.6% yield) of the desired product 43. m/z (APCI): 448 $[C_{24}H_{33}NO_7+H]^+$.

3-{3-[4-(4-Aminobutylphenoxy]-2-hydroxypropoxy}propane-1,2-diol (44)

A solution containing the compound 43 (0.15 g, 0.34 mmol) in ethanol (1.5 mL) was purged with nitrogen before and after the catalyst (0.15 g, 10% Pd/C, 50% wet) was added. The reaction mixture was placed under hydrogenation atmosphere for 45 min. The catalyst was vacuum filtered through diatomaceous earth and washed with ethanol (3×2 mL). The combined filtrates were concentrated under vacuum. The residue was chromatographed on silica gel, eluting with methanol/dichloromethane/concentrated ammonium (25/2.5/73.5, v/v), to afford the desired product 44 (0.053 g, 51% yield) as a colorless, viscous oil. $^1$H NMR (300 MHz, $CD_3OD$): δ 1.52 (m, 4H), 2.55 (t, 2H), 2.65 (t, 2H), 3.61 (m, 10H), 6.85 (d, 2H), 7.09 (d, 2H). m/z (APCI): 314 $[C_{16}H_{27}NO_5+H]^+$.

N-(3,5-Diamino-6-chloropyrazine-2-carbonyl)-N'-(4-{4-[3-(2,3-dihydroxypropoxy)-2-hydroxypropoxy]phenyl}butyl)guanidine (45, PSA 15143)

Compound 44 (50 mg, 0.159 mmol) was dissolved in a mixture of absolute ethanol (0.5 mL) and triethylamine (0.076 mL, 0.541 mmol) at 65° C. over 15 min. To the solution was added 1-(3,5-diamino-6-chloropyrazine-2-carbonyl)-2-methylisothiourea hydriodide (74 mg, 0.191 mmol). The reaction mixture was stirred at the above temperature for an additional 50 min, cooled down to ambient temperature and subsequently concentrated under vacuum. The residue was chromatographed on silica gel, eluting with methanol/dichloromethane/concentrated ammonium hydroxide (10/1/40, v/v) to afford the desired product 45 (53 mg, 36% yield) as a yellow solid. mp 73-82° C. (decomposed). $^1$H NMR (300 MHz, $CD_3OD$): δ 1.70 (m, 4H), 2.55 (m, 2H), 3.22 (m, 2H), 3.65 (m, 7H), 3.98 (m, 3H), 6.86 (d, 2H), 7.08 (d, 2H). m/z (APCI): 526 $[C_{22}H_{32}ClN_7O_6+H]^+$.

Example 12

Utilizing the procedures set forth above, the following capped pyrazinoylguanidine was prepared.

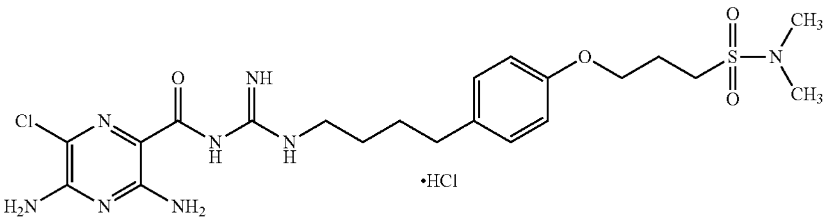

PSA 17927

| TEST | RESULT/REFERENCE |
|---|---|
| Description | Yellow solid |
| Identification: | |
| 300 MHz $^1$H NMR Spectrum (DMSO-$d_6$) | Consistent |
| Melting Point | 108-110° C. dec |
| HPLC Analysis | 96.5% (area percent), Polarity dC18 Column, Detector @ 220 nm |

-continued

| TEST | RESULT/REFERENCE |
|---|---|
| Miscellaneous Tests: | |
| ESI Mass Spectrum | m/z 465 $[C_{19}H_{25}ClN_8O_2S + H]^+$ |

-continued

| TEST | RESULT/REFERENCE |
|---|---|
| Miscellaneous Tests: | |
| ESI Mass Spectrum | m/z 527 $[C_{21}H_{31}ClN_8O_4S + H]^+$ |

Example 13

Utilizing the procedures set forth above, the following capped pyrazinoylguanidine was prepared.

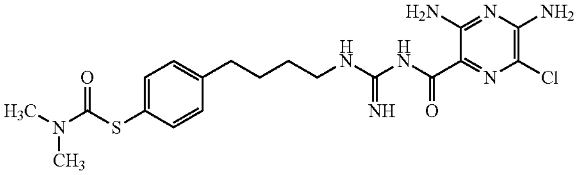

PSA 18211

| TEST | RESULT/REFERENCE |
|---|---|
| Description | Yellow solid |
| Identification: | |
| 300 MHz $^1$H NMR Spectrum (DMSO-d6) | Consistent |
| Melting Point | 153-155° C. dec |
| HPLC Analysis | 96.3% (area percent), Polarity dC18 Column, Detector @ 220 nm |

Example 14

Utilizing the procedures set forth above, the following capped pyrazinoylguanidine was prepared.

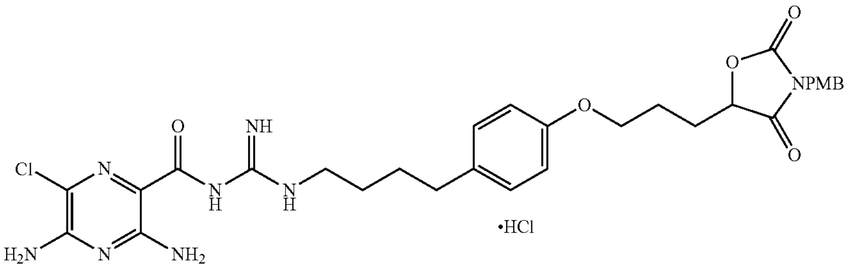

PSA 18212

| TEST | RESULT/REFERENCE |
|---|---|
| Description | Yellow solid |
| Identification: | |
| 500 MHz $^1$H NMR Spectrum ($CD_3OD$) | Consistent |
| Melting Point | 115-116° C. |
| HPLC Analysis | 97.1% (area percent), Polarity dC18 Column, Detector @ 220 nm |
| Miscellaneous Tests: | |
| ESI Mass Spectrum | m/z 639 [$C_{30}H_{35}ClN_8O_6$ + H]$^+$ |

Example 15

Utilizing the procedures set forth above, the following capped pyrazinoylguanidine was prepared.

PSA18229

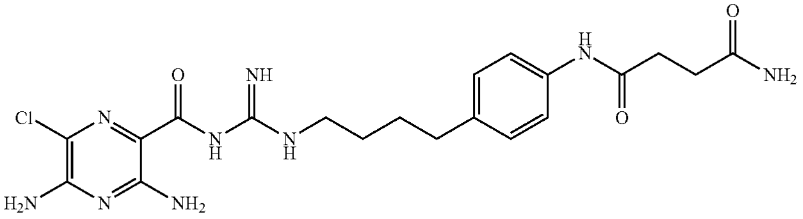

| TEST | RESULT/REFERENCE |
|---|---|
| Description | Yellow solid |
| Identification: | |
| 300 MHz $^1$H NMR Spectrum ($CD_3OD$) | Consistent |
| Melting Point | 190-192° C. |
| HPLC Analysis | 97.9% (area percent), Polarity dC18 Column, Detector @ 220 nm |
| Miscellaneous Tests: | |
| ESI Mass Spectrum | m/z 476 [$C_{20}H_{26}ClN_9O_3$ + H]$^+$ |

Example 16

Utilizing the procedures set forth above, the following capped pyrazinoylguanidine was prepared.

PSA18361

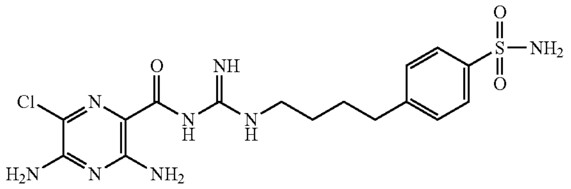

| TEST | RESULT/REFERENCE |
|---|---|
| Description | Yellow solid |
| Identification: | |
| 300 MHz $^1$H NMR Spectrum ($CD_3OD$) | Consistent |
| Melting Point | 124-126° C. dec |
| HPLC Analysis | 95.2% (area percent), Polarity dC18 Column, Detector @ 220 nm |
| Miscellaneous Tests: | |
| ESI Mass Spectrum | m/z 441 [$C_{16}H_{21}ClN_8O_3S$ + H]$^+$ |

Example 17

Utilizing the procedures set forth above, the following capped pyrazinoylguanidine was prepared.

PSA18592

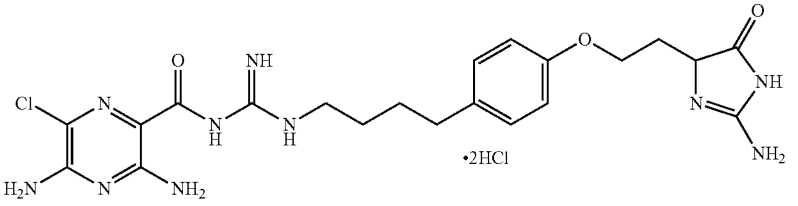

| TEST | RESULT/REFERENCE |
|---|---|
| Description | Yellow solid |
| Identification: | |
| 500 MHz $^1$H NMR Spectrum ($CD_3OD$) | Consistent |
| Melting Point | 189° C. dec |
| HPLC Analysis | 95.0% (area percent), Polarity dC18 Column, Detector @ 220 nm |
| Miscellaneous Tests: | |
| ESI Mass Spectrum | m/z 503 $[C_{21}H_{27}ClN_{10}O_3 + H]^+$ |

| TEST | RESULT/REFERENCE |
|---|---|
| Description | Pale Yellow solid |
| Identification: | |
| 300 MHz $^1$H NMR Spectrum ($CD_3OD$) | Consistent |
| Melting Point | 195-197° C. |
| HPLC Analysis | 97.4% (area percent), Polarity dC18 Column, Detector @ 220 nm |
| Miscellaneous Tests: | |
| ESI Mass Spectrum | m/z 477 $[C_{20}H_{25}ClN_8O_4 + H]^+$ |

Example 18

Utilizing the procedures set forth above, the following capped pyrazinoylguanidine was prepared.

Example 19

Utilizing the procedures set forth above, the following capped pyrazinoylguanidine was prepared.

PSA18593

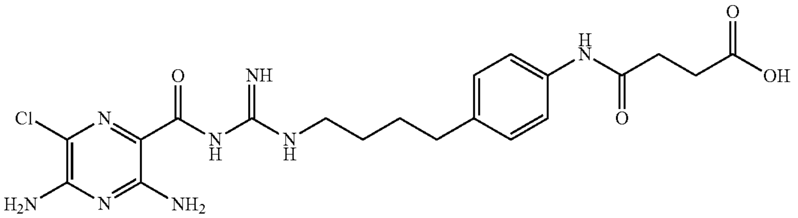

PSA19007

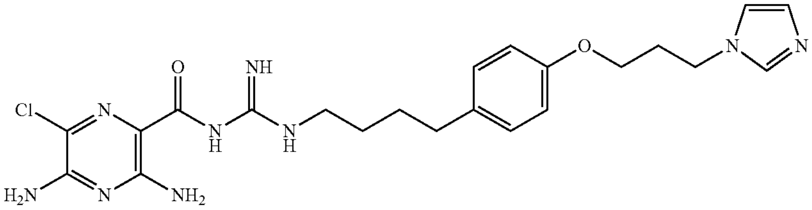

| TEST | RESULT/REFERENCE |
|---|---|
| Description | Yellow solid |
| Identification: | |
| 300 MHz $^1$H NMR Spectrum ($CD_3OD$) | Consistent |
| Melting Point | 210-212° C. dec |
| HPLC Analysis | 95.5% (area percent), Polarity dC18 Column, Detector @ 220 nm |
| Miscellaneous Tests: | |
| APCI Mass Spectrum | m/z 486 $[C_{22}H_{28}ClN_9O_2 + H]^+$ |

Example 20

Utilizing the procedures set forth above, the following capped pyrazinoylguanidine was prepared.

PSA 19912

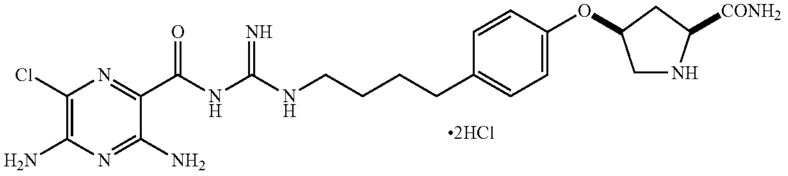

| TEST | RESULT/REFERENCE |
|---|---|
| Description | Yellow solid |
| Identification: | |
| 300 MHz $^1$H NMR Spectrum ($CD_3OD$) | Consistent |
| Optical Rotation | $[\alpha]^{25}_D$ −7.8° (c 0.46, Methanol) |
| Melting Point | 178-180° C. |

-continued

| TEST | RESULT/REFERENCE |
|---|---|
| HPLC Analysis | 97.0% (area percent), Polarity dC18 Column, Detector @ 220 nm |
| Miscellaneous Tests: | |
| ESI Mass Spectrum | m/z 490 $[C_{21}H_{28}ClN_9O_3 + H]^+$ |

Example 21

Utilizing the procedures set forth above, the following capped pyrazinoylguanidine was prepared.

PSA 24406

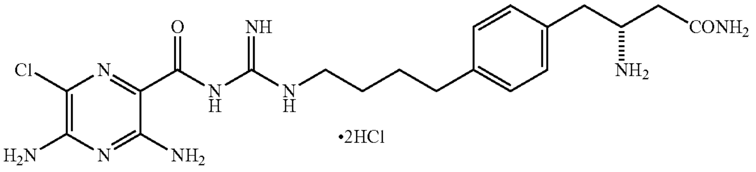

| TEST | RESULT/REFERENCE |
|---|---|
| Description | Yellow solid |
| Identification: | |
| 300 MHz $^1H$ NMR Spectrum ($CD_3OD$) | Consistent |
| Optical Rotation | $[\alpha]^{25}_D$ +0.5° (c 0.35, Methanol) |
| Melting Point | 215° C. |
| HPLC Analysis | 96.1% (area percent), Polarity dC18 Column, Detector @ 220 nm |
| Miscellaneous Tests: | |
| ESI Mass Spectrum | m/z 462 $[C_{20}H_{28}ClN_9O_2 + H]^+$ |

Example 22

Utilizing the procedures set forth above, the following capped pyrazinoylguanidine was prepared.

PSA24407

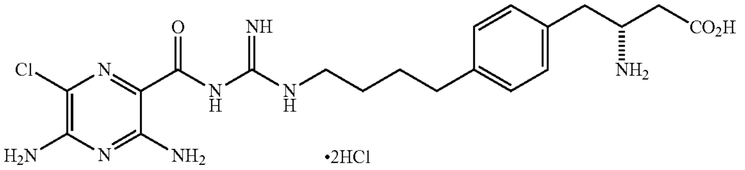

| TEST | RESULT/REFERENCE |
|---|---|
| Description | Yellow solid |
| Identification: | |
| 300 MHz $^1H$ NMR Spectrum ($CD_3OD$) | Consistent |
| Optical Rotation | $[\alpha]^{25}_D$ +4.1° (c 0.30, Methanol) |
| Melting Point | 230° C. dec |
| HPLC Analysis | 95.3% (area percent), Polarity dC18 Column, Detector @ 220 nm |
| Miscellaneous Tests: | |
| ESI Mass Spectrum | m/z 463 $[C_{20}H_{27}ClN_8O_3 + H]^+$ |

Example 23

Sodium Channel Blocking Activity of Selected Capped Pyrazinoylguanidines.

| PSA | $EC_{50}$(nM) | Fold Amiloride** (PSA 4022 = 100) |
|---|---|---|
| 15143 | 7 ± 3 (n = 3) | 107 ± 11 (n = 3) |
| 16208 | 11 ± 4 (n = 6) | 52 ± 21 (n = 6) |
| 16314 | 13 ± 2 (n = 4) | 41 ± 6 (n = 4) |
| 16313 | 15 ± 4 (n = 4) | 41 ± 7 (n = 4) |
| 16437 | 13 ± 7 (n = 7) | 77 ± 53 (n = 7) |
| 17482 | 16 ± 4 (n = 3) | 39 ± 6 (n = 3) |
| 17846 | 11 ± 6 (n = 4) | 104 ± 49 (n = 4) |
| 17926 | 25 ± 9 (n = 6) | 29 ± 12 (n = 6) |
| 17927 | 13 ± 4 (n = 3) | 83 ± 26 (n = 3) |
| 18211 | 10 ± 4 (n = 3) | 112 ± 52 (n = 2) |
| 18212 | 27 ± 17 (n = 4) | 32 ± 16 (n = 4) |
| 18229 | 15 ± 6 (n = 3) | 49 ± 15 (n = 3) |
| 18361 | 11 ± 4 (n = 3) | 76 ± 25 (n = 3) |
| 18592 | 8 ± 4 (n = 2) | 136 ± 58 (n = 2) |
| 18593 | 48 ± 16 (n = 6) | 13 ± 4 (n = 4) |
| 19007 | 18 ± 13 (n = 4) | 42 ± 17 (n = 4) |
| 19008 | 9 ± 1 (n = 4) | 54 ± 6 (n = 4) |
| 19912 | 26 ± 8 (n = 4) | 32 ± 10 (n = 4) |
| 23022 | 12 ± 3 (n = 4) | 79 ± 15 (n = 4) |
| 24406 | 8 ± 3 (n = 6) | 107 ± 38 (n = 6) |
| 24407 | 32 ± 11 (n = 10) | 23 ± 4 (n = 10) |
| 24851 | 28 ± 13 (n = 8) | 25 ± 10 (n = 8) |

**Relative potency for PSA 4022 = 100 using $EC_{50}$ from PSA 4022 in same run

Methods

Animal Preparation:

Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-Aerosol:

Aerosols of $^{99m}$Tc-Human serum albumin (3.1 mg/ml; containing approximately 20 mCi) were generated using a Raindrop Nebulizer which produces a droplet with a median aerodynamic diameter of 3.6 μm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of Activity at t-Zero):

A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t−4 hours):

The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paried t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

Obviously, numerous modifications and variations of the present invention are possible in light of the above teachings. It is therefore to be understood that within the scope of the appended claims, the invention may be practiced otherwise than as specifically described herein.

The invention claimed is:

1. A compound represented by formula (I):

(I)

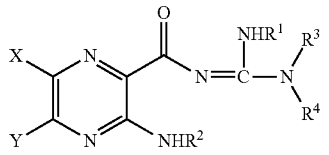

wherein

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxy, mercapto, lower alkoxy, lower alkyl-thio, halogen, lower alkyl, unsubstituted or substituted mononuclear aryl, or $—N(R^2)_2$;

$R^1$ is hydrogen or lower alkyl;

each $R^2$ is, independently, $—R^7$, $—(CH_2)_m—OR^8$, $—(CH_2)_m—NR^7R^{10}$, $—(CH_2)_m(CHOR^8)(CHOR^8)_n—CH_2OR^8$, $—(CH_2CH_2O)_m—R^8$, $—(CH_2CH_2O)_m—CH_2CH_2NR^7R^{10}$, $—(CH_2)_n—C(=O)NR^7R^{10}$, $—(CH_2)_n—Z_g—R^7$, $—(CH_2)_m—NR^{10}—CH_2(CHOR^8)(CHOR^8)_n—CH_2OR^8$, $—(CH_2)_n—CO_2R^7$, or

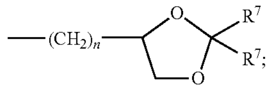

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that one of $R^3$ and $R^4$ is a group represented by formula (A):

(A)

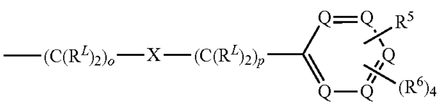

wherein each $R^L$ is, independently, $—R^7$, $—(CH_2)_n—OR^8$, $—O—(CH_2)_m—OR^8$, $—(CH_2)_n—NR^7R^{10}$, $—O—(CH_2)_m—NR^7R^{10}$, $—(CH_2)_n(CHOR^8)(CHOR^8)_n—CH_2OR^8$, $—O—(CH_2)_m(CHOR^8)(CHOR^8)_n—CH_2OR^8$, $—(CH_2CH_2O)_m—R^8$, $—O—(CH_2CH_2O)_m—R^8$, $—(CH_2CH_2O)_m—CH_2CH_2NR^7R^{10}$, $—O—(CH_2CH_2O)_m—CH_2CH_2NR^7R^{10}$, $—(CH_2)_n—C(=O)NR^7R^{10}$, $—O—(CH_2)_m—C(=O)NR^7R^{10}$, $—(CH_2)_n-(Z)_g—R^7$, $—O—(CH_2)_m—(Z)_g—R^7$, $—(CH_2)_n—NR^{10}—CH_2(CHOR^8)(CHOR^8)_n—CH_2OR^8$, $—O—(CH_2)_m—NR^{10}—CH_2(CHOR^8)(CHOR^8)_n—CH_2OR^8$, $—(CH_2)_n—CO_2R^7$, $—O—(CH_2)_m—CO_2R^7$, $—OSO_3H$, —O-glucose,

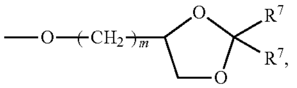

or

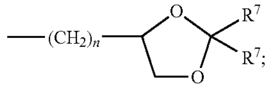

o is 0, 1, 2, 3, 4, 5, 6, 7, 8, 9 or 10;

p is 0, 1, 2, 3, 4, 5, 6, 7, 8, 9 or 10;

with the proviso that the sum of o and p is 1, 2, 3, 4, 5, 6, 7, 8, 9 or 10;

x is a single bond;

$R^5$ is Link-$(CH_2)_n$—CAP or Link-$(CH_2)_n$—$(Z)_g$—CAP;

Link is —$(CH_2)_n$— or —O—;

CAP is —$CR^{10}(Z_gR^{13})(Z_gR^{13})$, each $R^6$ is, independently, —$R^7$, —$OR^7$, —$OR^{11}$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(═O)$NR^7R^{10}$, —O—$(CH_2)_m$—C(═O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucose,

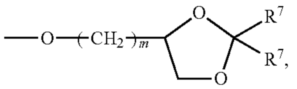

or

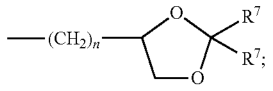

wherein when two $R^6$ are —$OR^{11}$ and are located adjacent to each other on a phenyl ring, the alkyl moieties of the two $R^6$ may be bonded together to form a methylenedioxy group;

each $R^7$ is, independently, hydrogen or lower alkyl;

each $R^8$ is, independently, hydrogen, lower alkyl, —C(═O)—$R^{11}$, 2-tetrahydropyranyl, or

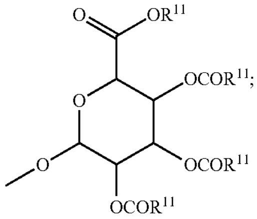

each $R^{10}$ is, independently, —H, —$CO_2R^{13}$, —C(═O)$NR^{13}R^{13}$, —C(═O)$R^{13}$, or —$(CH_2)_m$—$(CHOH)_n$—$CH_2OH$;

each Z is, independently, CHOH, C(═O), $CHNR^{13}R^{13}$, C═$NR^{13}$, or $NR^{13}$;

each $R^{11}$ is, independently, lower alkyl;

each $R^{13}$ is independently, hydrogen, $R^7$, $R^{10}$, —$(CH_2)_m$—$NR^{13}R^{13}$, —$(CH_2)_m$—$NR^{10}R^{10}$,

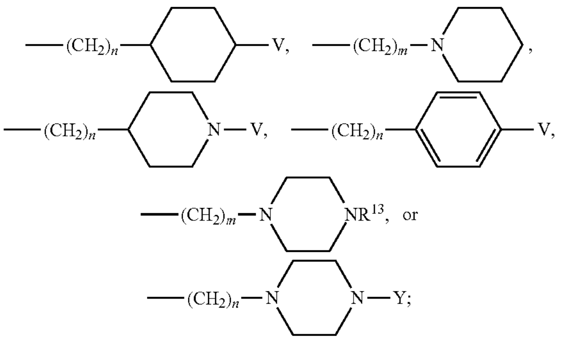

each g is, independently, 1, 2, 3, 4, 5 or 6;

each m is, independently, 1, 2, 3, 4, 5, 6 or 7;

each n is, independently, 0, 1, 2, 3, 4, 5, 6 or 7;

each Q is, independently, C—$R^5$ or C—$R^6$, wherein one Q is C—$R^5$;

each V is, independently, —$(CH_2)_m$—$NR^7R^{10}$ or —$(CH_2)_m$—$NR^7R^7$;

with the proviso that, when any two —$CH_2OR^8$ groups are located 1, 2 or 1,3- with respect to each other, the $R^8$ groups may be joined to form a cyclic mono- or di-substituted 1,3-dioxane or 1,3-dioxolane;

or a pharmaceutically acceptable salt thereof;

or a stereoisomer thereof.

2. The compound of claim 1 or pharmaceutically acceptable salt thereof, wherein X is chlorine, Y is —$NH_2$, $R^1$ is hydrogen, $R^2$ is hydrogen, $R^3$ is a group represented by formula (A), $R^4$ is hydrogen, and each $R^L$ is hydrogen.

3. The compound of claim 2 or pharmaceutically acceptable salt thereof, wherein the sum of o and p is 4.

4. The compound of claim 3 or pharmaceutically acceptable salt thereof, wherein each $R^6$ is hydrogen.

5. The compound of claim 4 or pharmaceutically acceptable salt thereof, wherein $R^5$ is Link-$(CH_2)_n$—CAP.

6. The compound of claim 4 or pharmaceutically acceptable salt thereof, wherein $R^5$ is Link-$(CH_2)_n$—$(Z)_g$—CAP.

7. The compound of claim 1 or pharmaceutically acceptable salt thereof, wherein each $R^{10}$ is, independently, —H or —$(CH_2)_m$—$(CHOH)_n$—$CH_2OH$.

8. The compound of claim 7 or a pharmaceutically acceptable salt thereof, wherein each $R^{13}$ is, independently, hydrogen or lower alkyl.

9. The compound of claim 1 or pharmaceutically acceptable salt thereof, wherein $R^3$ is hydrogen.

10. The compound of claim 1 or pharmaceutically acceptable salt thereof, which is in the form of a pharmaceutically acceptable salt.

11. The compound of claim 1 or pharmaceutically acceptable salt thereof, wherein Link is —$(CH_2)_n$—.

12. The compound of claim 1 or pharmaceutically acceptable salt thereof, wherein Link is —O—.

13. The compound of claim 1 or pharmaceutically acceptable salt thereof, wherein each $R^{10}$ is, independently, —C(═O)$NR^{13}R^{13}$.

14. The compound of claim 1 or pharmaceutically acceptable salt thereof, wherein each $R^{13}$ is, independently, hydrogen or lower alkyl.

15. The compound of claim 1 or pharmaceutically acceptable salt thereof, wherein each $R^{13}$ is hydrogen.

16. The compound of claim 1 or pharmaceutically acceptable salt thereof, wherein each $R^{13}$ is, independently, hydrogen, lower alkyl, $-(CH_2)_m-(CHOH)_n-CH_2OH$,

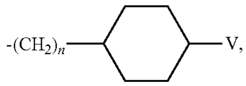,

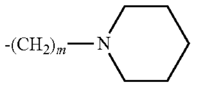,

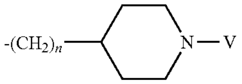

or

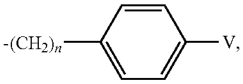, wherein V is $-(CH_2)_m-NR^7R^7$.

17. The compound of claim 1 or pharmaceutically acceptable salt thereof, wherein n is 1, 2, 3, 4, 5, 6 or 7.

18. A pharmaceutical composition, comprising the compound of claim 1 or pharmaceutically acceptable salt thereof and a pharmaceutically acceptable carrier.

19. A compound represented by formula (I):

(I)

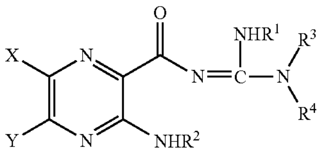

wherein

X is chlorine;

Y is $-NH_2$;

$R^1$ is hydrogen;

each $R^2$ is hydrogen;

$R^3$ is a group represented by formula (A):

(A)

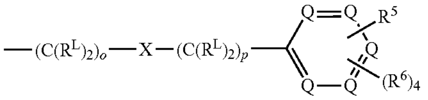

$R^4$ is hydrogen;

each $R^L$ is hydrogen the sum of o and p is 4;

x is a single bond;

$R^5$ is Link-$(CH_2)_n$—CAP;

Link is $-(CH_2)_n-$ or —O—;

CAP is $-CR^{10}(Z_gR^{13})(Z_gR^{13})$;

each $R^6$ is hydrogen;

wherein when two $R^6$ are $-OR^{11}$ and are located adjacent to each other on a phenyl ring, the alkyl moieties of the two $R^6$ may be bonded together to form a methylenedioxy group;

each $R^{10}$ is, independently, —H, $-CO_2R^{13}$, $-C(=O)NR^{13}R^{13}$, $-C(=O)R^{13}$, or $-(CH_2)_m-(CHOH)_n-CH_2OH$;

each Z is, independently, CHOH, C(=O), $CHNR^{13}R^{13}$, $C=NR^{13}$, or $NR^{13}$;

each $R^{11}$ is, independently, lower alkyl;

each $R^{13}$ is independently, hydrogen or $-(CH_2)_m-NR^{10}R^{10}$, each g is, independently, 1, 2, 3, 4, 5 or 6;

each m is, independently, 1, 2, 3, 4, 5, 6 or 7;

each n is, independently, 0, 1, 2, 3, 4, 5, 6 or 7;

each Q is, independently, $C-R^5$ or $C-R^6$, wherein one Q is $C-R^5$;

or a pharmaceutically acceptable salt thereof;

or a stereoisomer thereof.

* * * * *